US007301148B2

(12) United States Patent
Johnson

(10) Patent No.: US 7,301,148 B2
(45) Date of Patent: Nov. 27, 2007

(54) METHODS AND SYSTEMS FOR REMOTE DETECTION OF GASES

(75) Inventor: Timothy J. Johnson, Pasco, WA (US)

(73) Assignee: Battelle Memorial Institute, Richland, WA (US)

(*) Notice: Subject to any disclaimer, the term of this patent is extended or adjusted under 35 U.S.C. 154(b) by 432 days.

(21) Appl. No.: 10/422,027

(22) Filed: Apr. 23, 2003

(65) Prior Publication Data

US 2004/0211900 A1 Oct. 28, 2004

(51) Int. Cl.
*G01J 5/20* (2006.01)
(52) U.S. Cl. .................................... 250/338.4
(58) Field of Classification Search ............. 250/338.4
See application file for complete search history.

(56) References Cited

U.S. PATENT DOCUMENTS

| | | | |
|---|---|---|---|
| 3,662,171 A | | 5/1972 | Brengman et al. |
| 3,832,548 A | | 8/1974 | Wallack |
| 3,925,666 A | | 12/1975 | Allan et al. |
| 4,390,785 A | | 6/1983 | Faulhaber et al. |
| 4,496,839 A | | 1/1985 | Berstein et al. |
| 4,725,733 A | | 2/1988 | Horman et al. |
| 4,754,141 A | * | 6/1988 | Mindock ............ 250/343 |
| 4,795,253 A | | 1/1989 | Sandridge et al. |
| 4,999,498 A | | 3/1991 | Hunt et al. |
| 5,003,184 A | | 3/1991 | Hunt et al. |
| 5,130,544 A | | 7/1992 | Nilsson |
| 5,277,870 A | | 1/1994 | Fuller et al. |
| 5,294,796 A | | 3/1994 | Fee |
| 5,298,751 A | | 3/1994 | Fee et al. |
| 5,351,078 A | * | 9/1994 | Lemelson ............ 348/135 |
| 5,373,160 A | | 12/1994 | Taylor | |

(Continued)

FOREIGN PATENT DOCUMENTS

EP 0 235 404 A2 9/1987
WO WO 99/54700 10/1999

OTHER PUBLICATIONS

Herget, William F., Remote and Cross stack measurment of stack gas concentrations using a mobil FT-IR system, Feb. 15, 1982, Applied Optics, vol. 21, No. 4, pp. 635-641.*

(Continued)

*Primary Examiner*—David Porta
*Assistant Examiner*—Christine Sung
(74) *Attorney, Agent, or Firm*—Klarquist Sparkman, LLP

(57) ABSTRACT

Novel systems and methods for remotely detecting at least one constituent of a gas via infrared detection are provided. A system includes at least one extended source of broadband infrared radiation and a spectrally sensitive receiver positioned remotely from the source. The source and the receiver are oriented such that a surface of the source is in the field of view of the receiver. The source includes a heating component thermally coupled to the surface, and the heating component is configured to heat the surface to a temperature above ambient temperature. The receiver is operable to collect spectral infrared absorption data representative of a gas present between the source and the receiver. The invention advantageously overcomes significant difficulties associated with active infrared detection techniques known in the art, and provides an infrared detection technique with a much greater sensitivity than passive infrared detection techniques known in the art.

12 Claims, 11 Drawing Sheets

U.S. PATENT DOCUMENTS

| | | |
|---|---|---|
| 5,585,635 A | 12/1996 | Graham |
| 5,608,219 A | 3/1997 | Aucremanne |
| 5,650,624 A | 7/1997 | Wong |
| 5,656,813 A | 8/1997 | Moore et al. |
| 5,719,397 A | 2/1998 | Hallett et al. |
| 5,721,430 A | 2/1998 | Wong |
| 5,726,450 A | 3/1998 | Peterson et al. |
| 5,731,594 A * | 3/1998 | Kuroda et al. .......... 250/504 R |
| 5,734,165 A | 3/1998 | Unal et al. |
| 5,811,812 A | 9/1998 | Williams et al. |
| 5,831,267 A | 11/1998 | Jack et al. |
| 5,886,348 A | 3/1999 | Lessure et al. |
| 5,905,270 A | 5/1999 | McCaughey et al. |
| 6,097,034 A | 8/2000 | Weckstrom et al. |
| 6,100,529 A | 8/2000 | O'Dwyer et al. |
| 6,266,428 B1 | 7/2001 | Flanigan |
| 6,297,504 B1 | 10/2001 | Andreou |
| 6,373,056 B1 | 4/2002 | Johnson et al. |
| 6,396,577 B1 | 5/2002 | Ramstack |
| 6,507,309 B2 | 1/2003 | McMakin et al. |
| 6,518,562 B1 | 2/2003 | Cooper et al. |
| 6,525,814 B1 | 2/2003 | Hendrick, Jr. et al. |
| 6,545,278 B1 * | 4/2003 | Mottier et al. ......... 250/339.13 |
| 6,750,453 B1 * | 6/2004 | Nelson et al. ........... 250/338.5 |

OTHER PUBLICATIONS

Beil et al., "Detection of chemical agents in the atmosphere by passive IR remote sensing", Internal Standardization and Calibration Architectures for Chemical Sensors, Sep. 1999, Boston, MA, vol. 3856, pp. 44-56.

Esler et al., "Precision trace gas analysis by FT-IR spectroscopy. 1. Simultaneous analysis of $CO_2$, $CH_4$, $N_2O$, and CO in air", Anal. Chem., vol. 72, Jan. 2000, pp. 206-215.

Johnson et al., "Semiactive infrared remote sensing: a practical prototype and field comparison", Applied Optics, Jan. 2004, Opt. Soc. America, vol. 43, No. 3, pp. 638-650.

Knapp et al, "Ground-based passive FT-IR spectrometry", Vibrational Spectroscopy-Based Sensor Systems, Nov. 2001, Newton, MA, vol. 4577, pp. 269-286.

Tranchart et al., "Sensitive trace gas detection with near-infrared laser diodes and an integrating sphere", Applied Optics, Dec. 1996, Opt. Soc. America, vol. 35, No. 36, pp. 7070-7074.

* cited by examiner

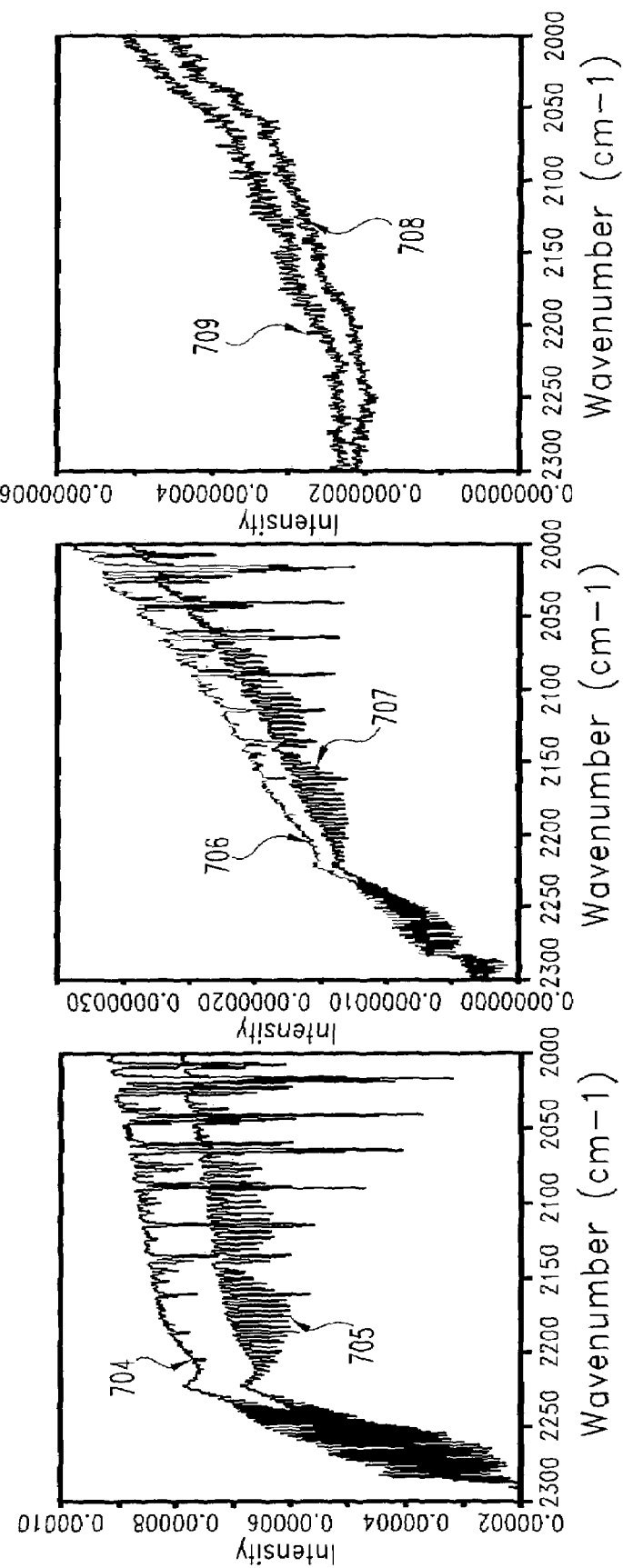

METHODS AND SYSTEMS FOR REMOTE DETECTION OF GASES

GOVERNMENT RIGHTS

This invention was made with Government support under Contract Number DE-AC06-76RL01830 awarded by the U.S. Department of Energy. The Government has certain rights in the invention.

BACKGROUND OF THE INVENTION

The present invention relates to systems and methods for remotely detecting at least one constituent of a gas via infrared detection. A system provided in accordance with the invention comprises at least one source of broadband infrared radiation and a spectrally sensitive receiver positioned remotely from the source. The source preferably features a surface having dimensions at least as large as the receiver's field of view at the distance separating the receiver and the source, and the source and the receiver are oriented such that the surface of the source is in the field of view of the receiver. The source includes a heating component thermally coupled to the surface, and the heating component is configured to heat the surface substantially uniformly to a temperature above ambient temperature. The receiver is operable to collect spectral infrared absorption data representative of a gas present between the source and the receiver. The system of the invention advantageously overcomes significant difficulties associated with active infrared detection techniques known in the art, and provides an infrared detection technique with a much greater sensitivity than passive infrared detection techniques known in the art.

As a background to the invention, much renewed emphasis has been placed in recent years on measuring trace gas constituents of the atmosphere, and researchers continually attempt to develop more sensitive methods to assess the state of the environment. Most countries now regulate or restrict atmospheric pollution and many have dedicated agencies (such as the EPA in the United States) to monitor gas-phase pollution levels. Hence, great emphasis is being given to developing reliable, near real-time sensor systems to monitor changes of industrial effluents. A variety of techniques have been described in the literature for using a Fourier Transform Infrared (FTIR) spectrometer for remote detection of a gas. Remote sensing with FTIRs roughly falls into two rather broad categories, namely, systems that are "active" in nature versus those that are "passive" in nature.

In an active system, the distinguishing characteristic is that there is an active source of infrared (IR) radiation, i.e., an artificial bright source of IR light, which is focused and collimated to provide a high-energy TR beam. Examples of active sources described in the literature include, for example, an SiC glow bar or a Nichrome wire element powered by a low-voltage high current DC source. The radiation is collimated using a telescope, and the beam is projected across the desired area and focused onto an IR detection system. In an alternative active method, called a monostatic setup, the source and detecting spectrometer stand together. The propagated IR beam is focused upon a remote retroreflector in a manner whereby the beam is reflected back to the receiver. The monostatic case is complicated by the fact that the returned beam must be precisely received by the receiver port in order to be focused onto the detector. In either case, active systems confer the advantage that the infrared detector sees a very large temperature difference between the background and the target gas plume (i.e., there is a hot active IR source). Typical sources may operate near 1350 Kelvin (K), and for measurements made near the earth's surface, ambient temperatures are near 275±40 K, thus providing a temperature contrast between sample and background of about 1000 K.

Although active FTIR spectroscopy offers excellent sensitivity, the logistics of trying to align the sender and receiver telescopes poses a serious problem. Successful employment of the active mode requires careful co-alignment of the IR sender and receiver telescopes, typically to better than 5 arc-sec. For a typical telescope clear aperture of about 25 cm (i.e., about 10 inches) and typical separations of 50 to 500 meters, it is extremely difficult to align the optical paths of the sender and receiver telescopes using commonly available mechanical means. Moreover, detection is only accomplished over the path defined by the set-up, and is not easy to readjust by angular sweeps because the sender and receiver telescope bores must not only be parallel, but must be co-axial as well, which can be difficult to achieve and maintain, usually requiring radio communication. Monitoring even a slightly different path requires a new alignment, which is cumbersome, requires remote communications, and is typically very time consuming, often requiring several hours. The analogy has been made that it is similar to "two rifles trying to shoot each other down the barrel," e.g. requiring alignment to better than 1 arc-min and approaching 2 to 5 arc-sec.

Maintaining both position and orientation is crucial in an active FTIR remote sensing system because an FTIR detector registers only the time-dependent modulation of intensity. As a consequence, even small arbitrary intensity fluctuations while recording the interferogram result in bogus features in the spectrum obtained from the FT algorithm. The active monostatic configuration combines the sender and receiver as a single bore-sighted unit with a retroreflector used to return the IR beam to the sender, alleviating many of the field alignment difficulties; however, sighting to the retroreflector within its FOV can still be formidable and the method presents other challenges for good signal recovery. Since the IR light does not emanate from a point source, the divergence of the beam can be a limiting factor since twice the nominal distance is covered, and the divergences of the outgoing and return beams seriously limit the radiation-gathering ability. At large separations the retro aperture(s) must be large to reduce their contribution to overall beam divergence. Finally, the outgoing and return beams also need to be separated; the simplest duplexing method is by a beam splitter, meaning that at best 25% of the light gathered from the source is seen by the detector. The divergence and reflective losses typically mean that less than about 10% of the gathered light is seen by the detector.

The alternative to the active IR detection method is passive FTIR spectroscopy for standoff detection of chemical signatures. The main advantage of the passive technique is that it has only a receiver optic and spectral sensor. There is no active source, which eases many logistical and operational requirements. The technique uses the ambient thermal radiation of the earth as the source of infrared light. If a gas cloud is at a temperature that is colder than the background temperature, an absorption signature is seen (provided the gas has an IR absorption spectrum, as most do). Should the gas temperature be greater than the background temperature, the chemical signature will be seen in emission mode. The passive configuration is sensitive for near real-time analysis because the detector (typically, a liquid $N_2$-cooled semiconductor at 77 K) is colder than the surroundings and is thus capable of detecting the incoming IR radiation. That is to say, since the detector is at about 80 K, and the earth is typically near 300 K, there may exist a difference in the radiometric output of the cloud and its background, and the detector is cold enough to register this difference. When the "on-plume" signature is seen in emission mode, the cloud is at a temperature hotter than the background temperature, and the chemical signature peaks are upward going, typically atop a broad spectral background due to the instrumental response. To remove the background and improve the sensitivity of the technique, an "off-plume" spectrum is normally recorded, and this is subtracted from the "on-plume" spectrum. This can be done simultaneously at the level of the interferogram providing more sensitive differencing. Ideally, the difference spectrum has a simple flat background with only the signature peaks visible. Should the background temperature be greater than the plume temperature, the same signatures are seen in absorption mode. Clearly, the temperature difference plays a crucial role in the nature of the signal and its sensitive recovery.

In either absorption or emission, however, the greatest limitation of the passive technique is usually the lack of significant thermal contrast between the plume and its background. Even when plume and background are at the same temperature it is theoretically possible to still measure the plume if its emissivity is significantly different from that of the background, because there is still a difference in radiance; however, in practice, the difference in emissivity of the background and foreground are similar in scale, so spectral brightness differences are hard to exploit. For passive FTIR there are some circumstances in which one can anticipate a large $\Delta T$ for passive sensing. For example, a stack emission could be known to be at a very high temperature, such as about 200° C., in relation to an ambient background. In many cases, however, this cannot be guaranteed, or stack-release temperatures can be highly variable, or possibly even intentionally changed. In such cases, it would be very advantageous to be able to guarantee a minimal thermal contrast that is as large as possible.

Most FTIR work exploits a narrow portion of the thermal IR spectral region. For example, passive remote sensing techniques are generally limited to the long-wave infrared (LWIR) atmospheric window in the 1300 to 700 $cm^{-1}$ (7 to 14 μm) range. The $CO_2$ band at 667 $cm^{-1}$ and many water rotational lines generally obscure the region below 700 $cm^{-1}$, while the water bending band centered at 1604 $cm^{-1}$ obscures much of the region from 1300 to 1900 $cm^{-1}$, thus leaving only a 700 to 1300 $cm^{-1}$ window for passive studies. Spectral information in the mid-IR is also useful, especially for monitoring CO and acid halides, but has very low ambient flux making passive detection of the molecules much less sensitive. Although passive FTIRs can monitor a wide diversity of compounds in the thermal IR (LWIR) atmospheric window, and therefore are a natural choice for air quality testing, they are not sensitive to acid halides and some light IR active gases such as NO or CO which are emitted by many exhaust stacks.

In view of the above background, it is apparent that there is a continuing need for further developments in the field of remote gas sensing using infrared detection. In particular, there is a need for further advancement in the development of techniques that are easy to use and provide a sensitivity that is capable of providing useful information to an operator. The present invention addresses these needs, and further provides related advantages.

SUMMARY OF THE INVENTION

Accordingly, the present invention provides novel systems and methods for remotely sensing at least one constituent of a gas via infrared detection. Inventive systems and methods avoid the difficulties associated with aligning two telescopes or separating a retro-reflected beam as are encountered in active IR detection systems, and provide much greater and more reliable sensitivity than passive IR detection systems.

In one aspect, the invention provides a system that comprises at least one source of broadband infrared radiation, and a spectrally sensitive receiver positioned remotely from the source. The source preferably features a surface having dimensions at least as large as the receiver's field of view at the distance separating the receiver and the source, and the source and the receiver are oriented such that the surface of the source is in the field of view of the receiver. The source preferably provides non-collimated broadband infrared radiation that fills the field of view of the receiver. The source includes a heating component thermally coupled to the surface, and configured to heat the surface to a temperature above ambient temperature. The receiver is operable to collect spectral infrared absorption data representative of a gas present between the source and the receiver.

In one embodiment of the invention, the system also includes means for comparing the data representative of the gas to known gas infrared absorption spectra to determine at least one characteristic of the gas. For example, the receiver can be operably coupled to a processing subsystem in which the known gas infrared absorption information is stored. The processing subsystem is operable to perform the comparison and display the comparison results to an operator. The receiver or the processing subsystem is preferably configured to generate an absorption spectrum representative of the gas. In one preferred embodiment, the receiver is a Fourier Transform Infrared spectrometer.

In another embodiment of the invention, the heating component is operatively coupled to a temperature controller. The temperature controller can be configured to receive input from a manual adjustment means, or can receive input from a remote location, for example through connection to a remote processing subsystem. In yet another alternate embodiment, the system includes a temperature sensor operable to sense ambient temperature. A system including a temperature sensor can be configured to control the heating component such that the heating component heats the surface to a temperature that is a predetermined number of degrees higher than ambient temperature sensed by the temperature sensor. In alternate embodiments, the temperature sensor, the temperature controller, the receiver, or combinations thereof are operatively coupled to a processing subsystem.

In yet another embodiment, the system also includes a second source of infrared radiation positioned at a second location remote from the receiver. The second source also includes a surface and a heating component thermally coupled to the surface, the heating component configured to heat the surface to a temperature above ambient temperature. The surface preferably has dimensions at least as large as the receiver's field of view at the second distance. The receiver is operable to collect spectral infrared absorption data representative of a second gas present between the second source and the receiver, and is configured for alternate positioning such that the surface of the first source and the surface of the second source are alternatively in its field of view. In one embodiment, the receiver is rotatably mounted upon a base; and the first and second sources are positioned such that the receiver is alternately rotatable from a first position in which the surface of the first source is in its field of view to a second position in which the surface of the second source is in its field of view, and from the second position to the first position. In still other embodiments, systems are provided that include one or more additional sources of infrared radiation at alternate positions, and the receiver is configured for repositioning to a position whereby the surface of the first source, the second source or the surface of one or more additional sources is in the field of view. The receiver is operable to alternately collect spectral infrared absorption data representative of a gas present between the receiver and the surface of the first source, a gas between the receiver and the surface of the second source, and a gas between the receiver and the surface of the one or more additional sources.

In another aspect of the invention, there is provided a system for remote monitoring of a gas that includes a plurality of spectrally sensitive receivers positioned at separate receiver locations. Each of the receivers includes an optical component defining a field of view. The system also includes at least one source of broadband infrared radiation, and optionally multiple sources, positioned remotely from each of the receivers. Each of the sources comprises a surface and a heating component thermally coupled to the surface; wherein the heating component is configured to heat the surface to a temperature above ambient temperature. Each receiver is positionable such that at least a portion of a source surface is in its field of view, and each of the receivers is operable to collect spectral infrared absorption data representative of a gas present between the respective receiver and the source. The system also can include a processing subsystem coupled to each of the receivers. The processing subsystem is operable to compare data from each receiver to information stored in the subsystem to provide comparison results to an operator. It is also optionally operable to perform multiple additional operations, or combinations thereof, including, for example, receiving temperature information from temperature sensors, calculating temperature differences, controlling heating components of the respective sources to adjust temperature differences, controlling movement of receivers, including movements to point the optical components to different sources and movements to optimize alignment, and the like.

The present invention also provides a novel method for remotely sensing at least one constituent of a gas. In one aspect, the invention provides a method including (1) providing a spectrally sensitive receiver at a receiver location, the receiver including an optical component defining a field of view; (2) providing an extended source of broadband infrared radiation at a source location separated from the receiver location, the source comprising a surface and a heating component thermally coupled to the surface; wherein the heating component is configured to heat the surface to a temperature above ambient temperature; and wherein the source and the receiver are oriented such that at least a portion of the surface of the source is in the field of view; (3) collecting spectral infrared absorption data with the receiver, the data being representative of a gas present between the source and the receiver; and (4) comparing the data representative of the first gas to known gas infrared absorption information to determine at least one characteristic of the first gas. In one manner of practicing the invention, the receiver is operably coupled to a processing subsystem operable to compare the data to information stored in the processing subsystem to an operator. In another manner of practicing the invention, the collecting comprises generating an absorption spectrum representative of the gas.

In another form of the invention, the method further includes (1) providing a second blackbody source of infrared radiation at a second source location remote from the receiver; (2) moving the receiver to a position whereby the second source is in the field of view; (3) collecting spectral infrared absorption data with the receiver, the data being representative of a second gas present between the second source and the receiver; and (4) comparing the data representative of the second gas to known gas infrared absorption information to determine at least one characteristic of the second gas. In still another embodiment, the method further includes alternately aligning the receiver with the surface of the first source such that the surface is in the field of view and with the surface of the second source such that the second source is in the field of view, and repeating the collecting and comparing at the alternate positions at predetermined intervals. In still other embodiments, the method further includes providing one or more additional sources of infrared radiation at alternate positions; alternately aligning the receiver with the surface of the first source, the second source and one or more additional sources; and repeating the collecting and comparing at the alternate positions at predetermined intervals.

In an alternate manner of practicing the invention, there is provided a method for remotely analyzing a gas that includes: (1) obtaining spectral infrared absorption data from a spectrally sensitive receiver, the data being representative of a gas present between the receiver and a remotely positioned extended source of broadband infrared radiation; and (2) comparing the data to known infrared absorption spectra to determine at least one characteristic of the gas; wherein the source includes a surface thermally coupled to a heating component, the heating component configured to heat the surface to a temperature above ambient temperature; wherein the receiver includes an optical component defining a field of view; and wherein the receiver is oriented such that at least a portion of the surface is in the field of view.

The invention also provides a method for remotely analyzing a gas that includes (1) providing a spectrally sensitive receiver at a receiver location, the receiver including an optical component defining a field of view; (2) providing an extended source of broadband infrared radiation at a source location separated from the receiver location, the source comprising a surface and a heating component thermally coupled to the surface; wherein the source and the receiver are oriented such that at least a portion of the surface is in the field of view; and wherein the heating component is configured to heat the surface to a temperature at which the surface emits sufficient infrared radiation in the MWIR region of from about 1850 to about 2300 $cm^{-1}$ to produce a detectable signal in the MWIR region when a gaseous compound that absorbs radiation in the MWIR region is present; (3) collecting spectral infrared absorption data with the receiver, the data being representative of a gas present between the source and the receiver; and (4) comparing the data representative of the first gas to known gas infrared absorption information to determine at least one characteristic of the first gas.

Inventive systems and methods offer superior sensitivity to passive methods by providing a guaranteed large thermal contrast, while minimizing the significant alignment and stability impediments of the active measurements.

Further forms, embodiments, objects, features, and aspects of the present invention shall become apparent from the description contained herein.

BRIEF DESCRIPTION OF THE FIGURES

FIGS. 10-12 set forth sample and background spectra in the MWIR for each of the three different techniques: telescope TL19 (FIG. 10), griddle GR19 (FIG. 11), and sky SK19 (FIG. 12). Note the relative changes of y-axis signal intensity, as seen in FIG. 9. The background spectra have been vertically offset for clarity. The CO band is centered at 2143.3 cm$^{-1}$.

DESCRIPTION OF THE PREFERRED EMBODIMENTS

For the purpose of promoting an understanding of the principles of the invention, reference will now be made to preferred embodiments and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention provides novel systems and methods for remotely detecting at least one constituent of a gas via infrared detection. A system provided in accordance with the invention comprises at least one extended source of broadband infrared radiation and a spectrally sensitive receiver positioned remotely from the source. The receiver is operable to collect spectral infrared absorption data representative of one or more gas present between the source and the receiver. As used herein, the term "extended" is used to indicate that the source has a radiation-emitting surface that has dimensions of sufficient size to fill a significant portion the field of view of the receiver during operation of the system, i.e., at a specified distance between source and receiver. In one preferred embodiment, the dimensions of the surface are of sufficient size to fill at least about 50% of the field of view of the receiver during operation of the system, more preferably at least about 75%, and still more preferably 100% of the field of view. An extended source, in contrast to a point source, does not require collimating optical equipment to broaden its dimensions in order to be suitable for use in connection with the invention. The source is a preferably a broadband source. In addition, the source is preferably a blackbody source. As used herein, the term "blackbody" is intended to refer to a characteristic of a surface whereby a majority of incident infrared radiation is absorbed by the surface. The source also preferably has a relatively high emissivity, i.e., an emissivity approaching 1.0. The system of the invention overcomes significant difficulties associated with active infrared detection techniques known in the art, and provides an infrared detection technique with a much greater sensitivity than passive infrared detection techniques known in the art.

Figure 1:
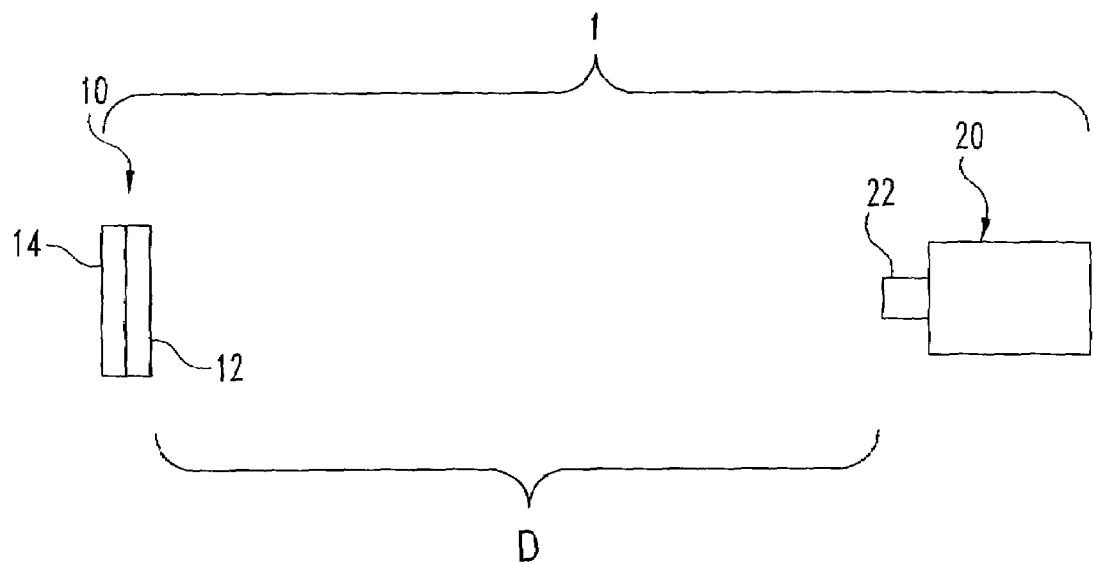
FIG. 1 is a schematic plan view diagram of one embodiment of a remote gas detection system according to the present invention.

In an inventive system, such as system 1 set forth in FIG. 1, source 10 is positioned at a distance D from receiver 20. Source 10 includes surface 12 and heating component 14 thermally coupled to surface 12. Heating component 14 is configured to heat surface 12 to a temperature above ambient temperature. Heating component 14 preferably heats surface 12 substantially uniformly. The term "substantially uniformly" is used herein to refer to a uniformity of heating whereby the temperatures of different areas of the surface do not vary by more than about 30° C. The temperatures of different areas of the surface more preferably do not vary by more than about 20° C., still more preferably by more than about 10° C. While not necessary to the practice of the invention, the surface in a preferred embodiment is a substantially flat surface.

In one embodiment of the invention, distance D between the infrared source and the receiver is at least about 5 meters. In another embodiment, the distance D is from about 20 meters to about 300 meters. In yet another embodiment, the source is positioned from about 40 to about 250 meters from the receiver. In still another embodiment, the source is spaced from about 50 to about 200 meters from the receiver. In one preferred embodiment, the distance is from about 75 to about 125 meters. It is, of course, understood that the present invention is also suitable for use where alternative distances separate the source and the receiver, and it is within the purview of a person of ordinary skill in the art, in view of the present description, to select a suitable distance for a given application.

Although it is not intended that the invention be limited by the type of heating component selected for use in accordance with the invention, one example of a heating component that finds advantageous use is an electric heating element as found in many household cooking appliances, such as, for example, a pancake griddle. Indeed, in prototype testing of the present invention, described in the Examples, the source selected for use in the inventive prototype was a modified commercial pancake griddle. It is, of course, not intended that the invention be limited to a heating component of this type. Another type of heating component that is contemplated by the invention is a radiator-type component defining flow paths for passing heated fluid in thermal contact with the surface, thereby heating the surface. In some applications of the invention, the heating component could utilize heated water. In other applications, for example, where heating to higher temperatures is required, use of an oil as the heating fluid may be desired. It is well within the purview of a person of ordinary skill in the art to select and use a suitable heating component in the practice of the invention.

In one embodiment of the invention, the surface is heated to a temperature of from about 10 to about 300° C. higher than ambient temperature at the location of the detection system. In another embodiment the temperature of the surface is from about 20 to about 200° C. higher than ambient temperature. In yet another embodiment, the temperature of the surface is from about 50 to about 150° C. higher than ambient temperature. In still another embodiment, the temperature of the surface is from about 75 to about 125° C. higher than ambient temperature. It is understood that the sensitivity of the absorbance data obtained from the inventive system, and thus the ability of the system to detect compounds at low concentrations, directly correlates with the temperature differential between the source and a gas between the source and the receiver. It is therefore not intended that the invention be limited to the above examples, but rather include other temperatures that are suitable for achieving the advantageous result of the invention, as would occur to a person of ordinary skill in the art.

Figure 2:
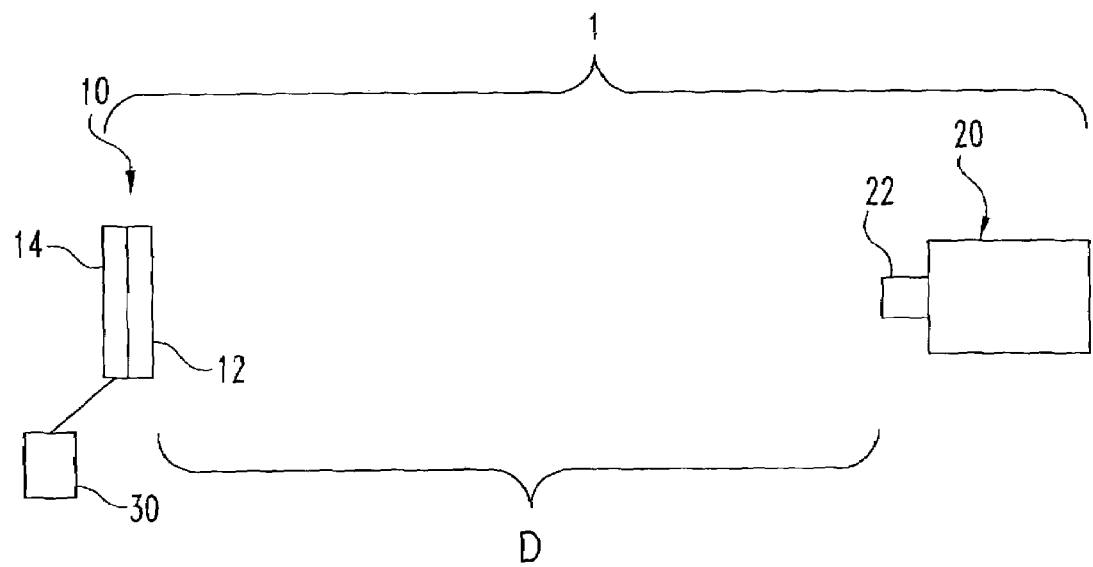
FIG. 2 is a schematic plan view diagram of another embodiment of a remote gas detection system according to the present invention.

In another embodiment of the invention, depicted schematically in FIG. 2, heating component 14 is operatively coupled to a temperature controller 30. Temperature controller 30 can be of the type that is manually adjustable by a system operator, or of a type that is responsive to other types of input. Temperature controller 30 shown in FIG. 3 includes ambient temperature sensor 32, and is operative to receive ambient temperature information from temperature sensor 32 and control heating component 14 such that heating component 14 heats surface 12 to a substantially uniform temperature that is a predetermined number of degrees higher than ambient temperature sensed by temperature sensor 32. Alternatively, ambient temperature sensor 32 can be independent of temperature controller 30 in other embodiments, or can be absent. Temperature controller 30 will typically include a thermostat configured to maintain the surface at a desired temperature, but may alternatively include other mechanisms for achieving temperature control. Source 10 can also optionally include one or more surface temperature sensors 34 for monitoring the temperature of surface 12 at one or more locations if desired.

Receiver 20 is preferably of a type capable of generating an absorption spectrum, i.e., a spectrum depicting absorbance information for infrared radiation at multiple selected wavelengths. Such a receiver will typically include an optical component 22, often referred to as a "telescope," for focusing infrared radiation into a high energy beam, and components for measuring the relative intensity of radiation at selected wavelengths. The receiver is also capable of generating an absorbance spectrum from the measured radiation, thus depicting an absorbance value of a particular gas at each of the selected wavelengths. A particularly preferred receiver for use in accordance with the invention is a Fourier Transform Infrared spectrometer. A wide variety of alternative receivers having this type of capability, such as, for example, dispersive spectrometers and radiometers, can also be used, and a person of ordinary skill in the art can readily select a suitable receiver for use in an inventive system.

Heated surface 12 of source 10 preferably has dimensions at least as large as the field of view of receiver 20 at the distance D separating the source and the receiver. Thus, when distance D is relatively large, the desired surface dimensions are larger than if the distance D is smaller. In operation, the source and the receiver are oriented such that the heated surface of the source is in the field of view of the receiver. When oriented in this manner, infrared radiation emitted by the source passes to the receiver as non-collimated radiation. Because the radiation is non-collimated, the alignment of the source and receiver is very simple, requiring only the placement of the source surface in the field of view of the receiver, preferably with the surface at least approximately normal to the receiver's line of sight.

When the source and receiver are oriented as described, spectral infrared absorption data is collected that is representative of a gas present between the source and the receiver. This data can then be compared to known gas infrared absorption information to determine characteristics of the gas, such as, for example, to determine whether an extraneous gas is present in the atmosphere. It is, of course, understood that anomalies in the spectrum can be detected, such as, for example, where a foreign gas is present in the atmosphere, even if the identity of the foreign gas is not identifiable, i.e., is a gas for which an infrared absorption spectrum has not been previously obtained. It is, of course, understood that the invention is useful even if the identity of the gas is not immediately determinable, because it can alert the operator to the presence of an unknown gas in the atmosphere.

It is expected that, more commonly, the invention will allow the specific determination of the identity of a foreign gas by comparison to previously-obtained spectral data for a plurality of gases. For example, to maximize the utility of the invention, IR spectra are obtained for a wide variety of foreign gases envisaged as being potentially present in a location, and these spectra are used as reference spectra. Spectra obtained during operation of the invention can then be compared to the reference spectra for determination of the identity of the foreign gas. In one preferred manner of practicing the invention, the reference spectra information is stored in memory included in a processing subsystem associated with the receiver, or in memory accessible by such a processing subsystem.

Figure 3:
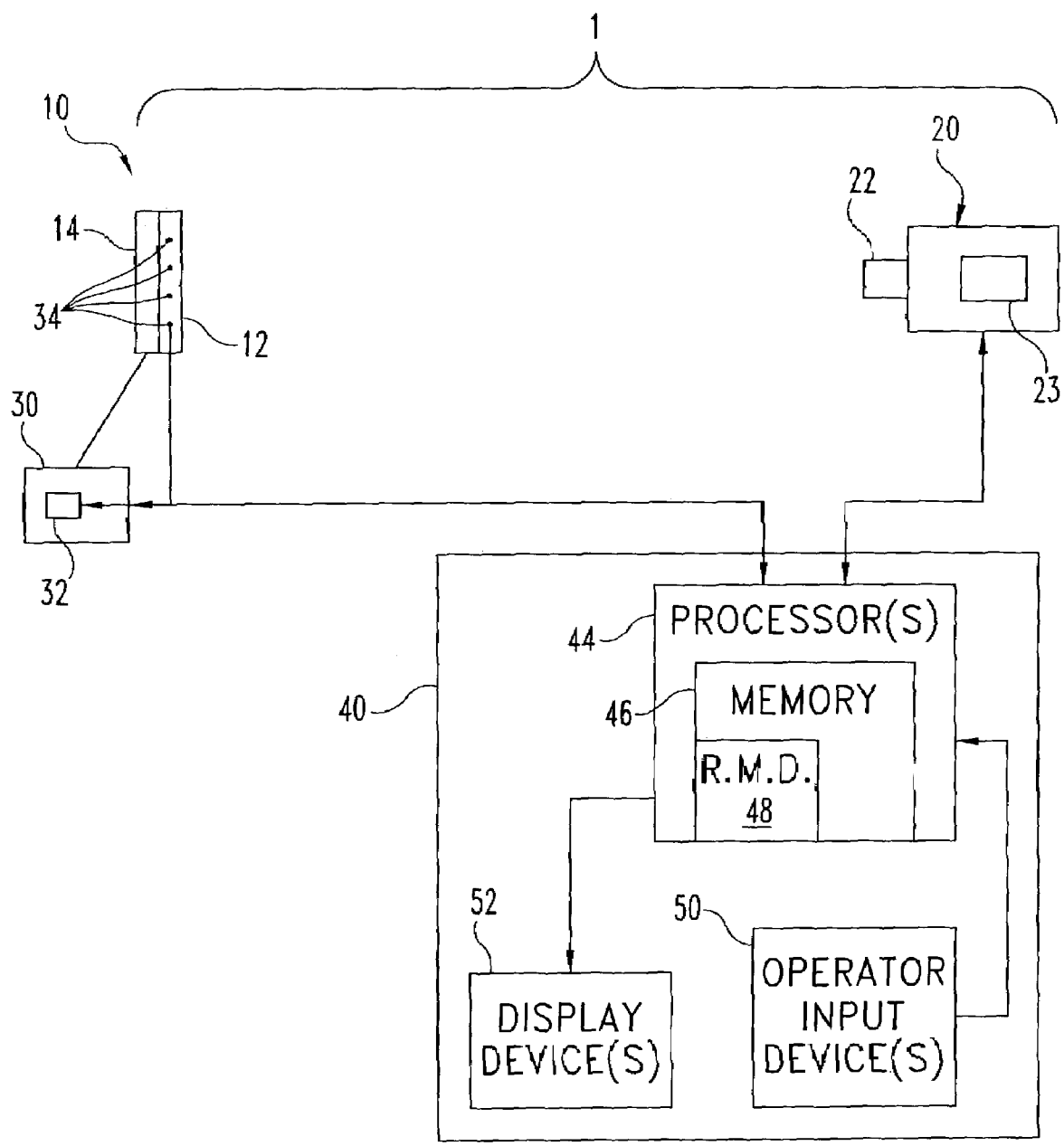
FIG. 3 is a schematic plan view diagram of another embodiment of a remote gas detection system according to the present invention.

In one preferred system, as depicted schematically in FIG. 3, receiver 20 is operably coupled to processing subsystem 40. Receiver 20 provides data corresponding to the gas present between source 10 and receiver 20 to one or more processors 44 of subsystem 40 so that the data can be compared to reference spectra information stored in memory 46 or elsewhere. The comparison results can be presented to an operator visually with a display, aurally with a loudspeaker, and/or using such other types of output devices as would occur to those skilled in the art. In this manner, information regarding the identity and concentration of the gas between source 10 and receiver 20 is provided rapidly, so that, if a foreign gas is present, the information can be communicated to allow the operator to take appropriate steps in response.

Processor(s) 44 can be comprised of one or more components of any type suitable to process the data received from receiver 20, including digital circuitry, analog circuitry, or a combination of both. Processor(s) 44 may be comprised of one or more components configured as a single unit, or when of a multi-component form, processor(s) 44 may have one or more components remotely located relative to the others, or otherwise have its components distributed throughout inventive system 1. Processor(s) 44 can be of a programmable type; a dedicated, hardwired state machine; or a combination of these. For a multiple processor form, distributed, pipelined, and/or parallel processing can be utilized as appropriate. In one arrangement, an integrated circuit form of a programmable digital signal processor is utilized.

Memory 46 is included in processor(s) 44, and is arranged for reading and writing of data in accordance with one or more routines executed by processor(s) 44. Memory 46 can be of a solid-state variety, electromagnetic variety, optical variety, or a combination of these forms. Furthermore, memory 46 can be volatile, nonvolatile, or a mixture of these types. Memory 46 can be at least partially integrated with processor(s) 44. Removable processor-readable Memory Device (R.M.D.) 48 is also included with processor(s) 44. R.M.D. 48 can be a floppy disc, cartridge, or tape form of removable electromagnetic recording media; an optical CD or DVD disc; an electrically reprogrammable solid-state type of nonvolatile memory, and/or such different variety as would occur to those skilled in the art. In still other embodiments, R.M.D. 48 is absent. Besides memory, processor(s) 44 may include any oscillators, control clocks, interfaces, signal compensators/conditioners, filters, limiters, Analog-to-Digital (A/D) converters, Digital-to-Analog (D/A) converters, communication ports, or other types of components/devices as would occur to those skilled in the art to implement the present invention.

Subsystem 40 also includes one or more operator input devices 50 and one or more display devices 52. Operator input device(s) 50 can include a keyboard, mouse or other pointing device, a voice recognition input subsystem, and/or a different system as would occur to those skilled in the art. Operator display device(s) 52 can be of a Cathode Ray Tube (CRT) type, Liquid Crystal Display (LCD) type, plasma type, Organic Light Emitting Diode (OLED) type, or such different type as would occur to those skilled in the art. In one form, at least a standard keyboard and mouse are included in input device(s) 50, and at least one high-resolution color graphic display is included in display device(s) 52.

Processing subsystem 40 can also optionally be coupled to a communication subsystem (not shown) that includes a network server coupled to a computer network, which optionally includes the internet. A communication link can be provided in the form of one or more dedicated communication channels for subsystem 40, a Local Area Network (LAN), and/or a Wide Area Network (WAN), such as the internet. In other words, a server can be remotely located relative to subsystem 40 with the computer network providing the link. Indeed, in one embodiment, a server is coupled to a number of remotely located subsystems with corresponding receivers. In still other embodiments, more than one server can be coupled to a common receiver and subsystem 40 arrangement.

Temperature controller 30 and temperature sensor 32, whether integrated or separate, can optionally be connected to subsystem 40 in a manner whereby temperature information, i.e., ambient temperature information and/or source surface temperature information, is communicated to subsystem 40. Subsystem 40 is able to display this information to an operator of the system, and/or use the information to adjust the temperature of source 10 or in algorithms used to make comparisons of infrared absorbance data from the receiver to reference spectra. The surface temperature information can be used, for example, in algorithms for determining the concentration of a give gaseous compound in the atmosphere. In an embodiment including ambient temperature sensor 32, ambient temperature information can be used by processor(s) 44 to determine a desired surface temperature. Alternatively, or in addition, subsystem 40 can be configured to directly control temperature controller 30 based upon predetermined parameters to thereby control IR emission characteristics of source 10. As another alternative, temperature controller can be connected to a separate processor or processing subsystem (not shown) for independent control of temperature controller 30, or may be controlled in other manners as described herein.

Figure 4:
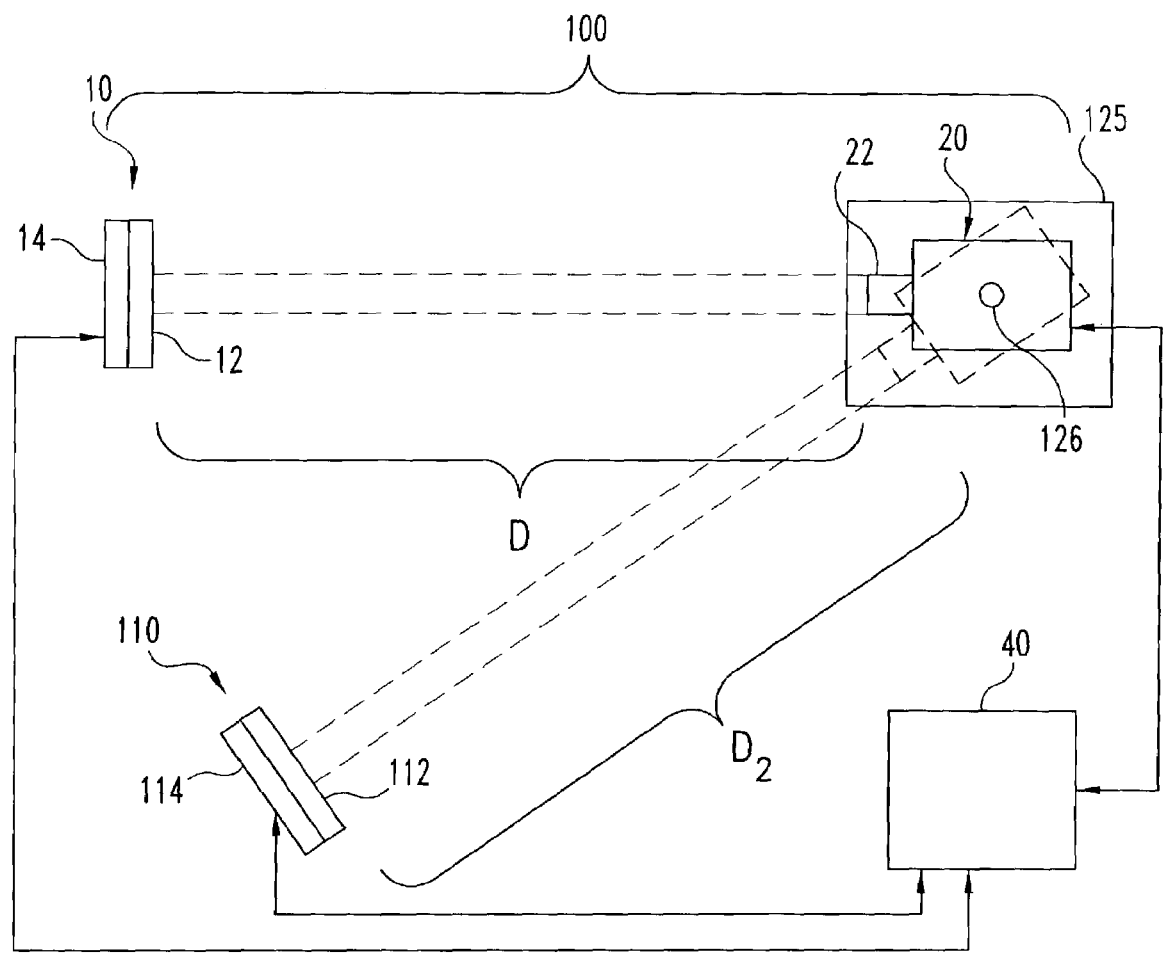
FIG. 4 is a schematic plan view diagram of another embodiment of a remote gas detection system according to the present invention, featuring multiple IR sources.

Another advantage of the present invention is that it provides the capability of readily creating additional test paths for testing the atmosphere or other gaseous system in multiple locations. In this regard, in another embodiment of the invention, depicted schematically in FIG. 4, a second source 110 is positioned at a second location separated from receiver 20 by a second distance $D_2$. The second source includes a surface 112 and a heating component 114 thermally coupled to surface 112 and configured to heat the surface to a temperature above ambient temperature. The surface 112 of the second source 110 preferably has dimensions at least as large as the field of view of the receiver 20 at the second distance $D_2$. The receiver 20 is configured for repositioning to a position whereby the surface of the second source 110 is in the field of view. In this manner, the receiver is operable to collect spectral infrared absorption data representative of a second gas present between the second source 110 and the receiver 20. A person of ordinary skill in the art will readily appreciate that the system depicted in FIG. 4 can be used to detect gases at multiple locations by alternately positioning the receiver such that the first source 10 is in its field of view, and collecting spectral infrared absorption data representative of a first gas between the receiver 20 and the first source 10; then positioning the receiver such that the second source 110 is in its field of view, and collecting spectral infrared absorption data representative of a second gas between the receiver 20 and the second source 110: and repeating as desired. After collecting spectral infrared absorption data at each location, the data can be compared to known gas infrared absorption information to determine at least one characteristic of the respective gases, as described above, at discreet points in time.

It is readily appreciated that additional sources of infrared radiation can be provided at additional alternate positions to provide inventive systems that are capable of remotely detecting gases at a wide variety of positions about the receiver. Thus, in an inventive system with multiple sources, the receiver can be sequentially pointed to multiple sources, such that each source is in the field of view of the receiver for a period of time sufficient to collect spectral infrared absorption data representative of a gas therebetween. In a particularly preferred system, the receiver is rotatably mounted upon a base, such as base 125 depicted in FIG. 4, for example, using a swivel component 126, and the sources are positioned such that the receiver can simply be rotated about the swivel component to a plurality of positions in which alternate sources are in the field of view of the receiver. In a system in which the heated surface of the source is larger than the field of view of the receiver, the inventive system is remarkably easy to align and use. The receiver optics are simply pointed toward the source, and the system is then ready for use as described herein. This allows the rapid realignment of the receiver to monitor gases in multiple locations in quick succession. Although not necessary to the practice of the invention, in one embodiment, receiver 20 includes an automatic alignment mechanism 23, as shown schematically in FIG. 3, to aid in positioning receiver 20 in an orientation whereby source is within the field of view of receiver 20. For example, a skilled artisan will appreciate that a feedback mechanism can be used in which separate motors are used to incrementally move the field of view in the vertical and horizontal directions respectively while measuring signal strength at each incremental position. Incremental movement continues until a position is reached at which the signal strength is maximized, at which point the field of view is determined to be optimally aligned upon source 10. A person of ordinary skill in the art will readily appreciate that processing subsystem 40 can be used to control major movements of receiver 20 between predetermined positions, such as between positions at which different sources are placed in receiver's field of view, by coupling subsystem 40 to a motor to selectively control receiver movement. Subsystem 40 can also be used to control minor movements of alignment mechanism 23.

Figure 5:
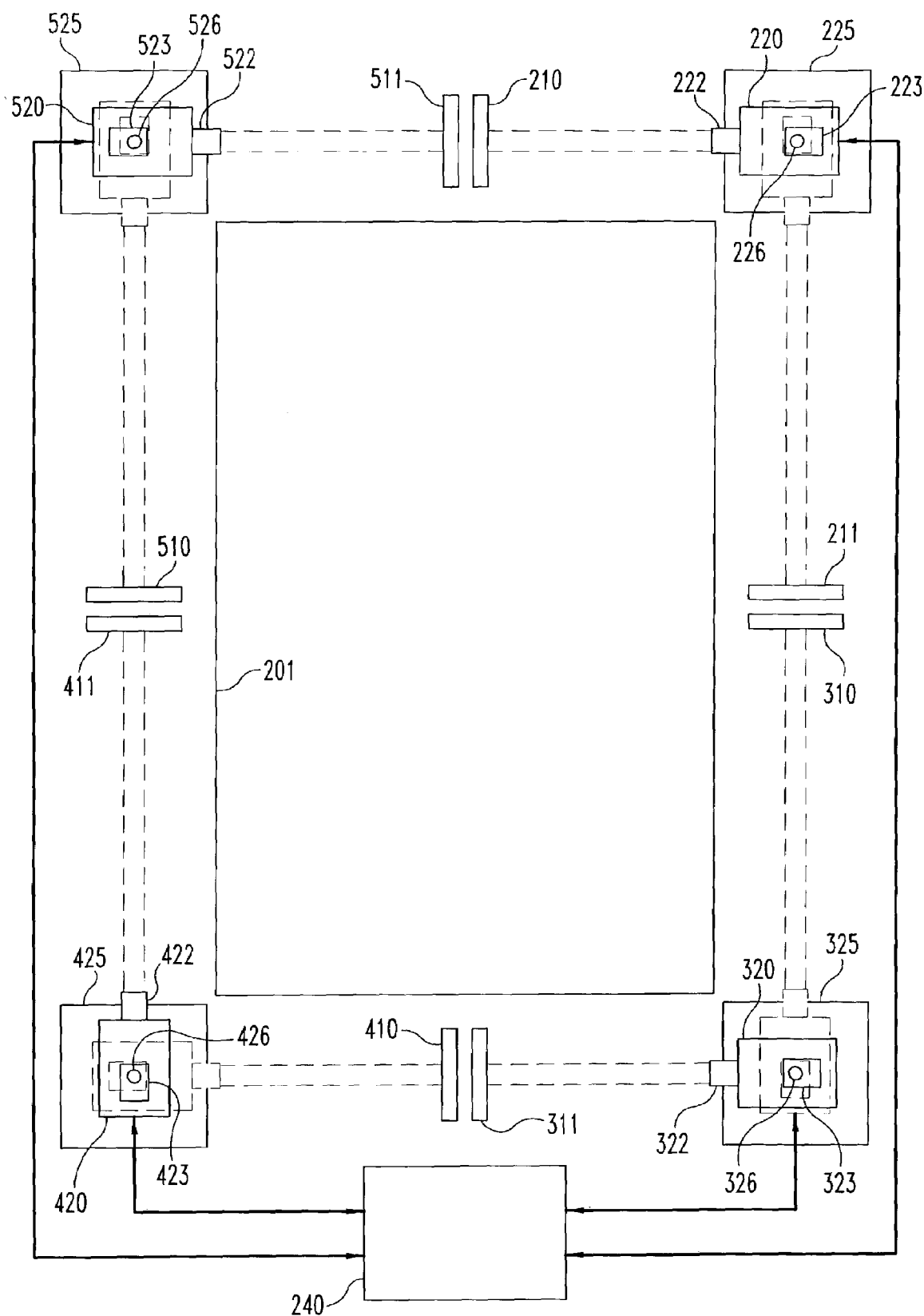
FIG. 5 is a schematic plan view diagram of another embodiment of a remote gas detection system according to the present invention, featuring multiple receivers and multiple IR sources.

Given a sufficiently powerful computing system for comparing absorbance data to reference spectra, it is seen that an inventive system can rapidly monitor a large area for foreign gases in a very short period of time, and can continue to periodically monitor the area over a long period of time. An exemplary system is depicted in FIG. 5, in which an inventive system is configured to test gases around perimeter 201, which can represent a perimeter around any area to be monitored, such as, for example, a school, a hospital, a military installation, or the like. In this system, receivers 220, 320, 420, 520 are positioned at corners of perimeter 201, and each receiver is configured to pivot about swivel components 226, 326, 426, 526, respectively to monitor alternate perimeter locations. For example, receiver 220 is oriented such that it is movable between a position at which source 210 is in its field of view to a position at which source 211 is in its field of view. Likewise, receiver 320 can be alternately pointed to source 310 and 311, receiver 420 can be alternately pointed to source 410 and source 411, and receiver 520 can be alternately pointed to source 510 and source 511. In this embodiment, processing subsystem 240 is coupled to receivers 220, 320, 420, 520 to provide the advantages described above. Subsystem 240 can also be coupled to temperature sensors (not shown), temperature controllers (not shown), communications interfaces (not shown) and the like as would occur to a person skilled in the art in view of the present specification. In this manner, large perimeters can be continuously monitored for the presence of foreign gases. The inventive system is particularly suited for automated control. The system is readily configured to provide for automatic rotation and detection steps, which can be controlled in accordance with a pre-programmed sequence of steps. It is well within the purview of a person of ordinary skill in the art to program an inventive system that is capable of following such a sequence, collecting spectral data, making data comparisons, and recording and/or transmitting information regarding the gas or gases to an operator located proximal to or remote from the receiver.

A person of ordinary skill in the art will appreciate that a remote detection system as described herein provides significant advantages over passive remote detection systems described in the prior art by creating a relatively large temperature difference for the plume versus the background, thus guaranteeing a much higher probability of foreign gas detection. A prototype system of the present invention has been used to make a direct comparison of the relative sensitivities of the inventive system to a conventional passive detection system and a conventional active detection system. Using identical acquisition times and parameters, and using carbon monoxide as the subject analyte, a direct comparison was made between the sensitivity of the techniques. Such a sensitivity comparison cannot cover all possible scenarios, as the results will depend on the wavelength region, sample of interest, and several measurement conditions, such as the plume and background temperatures; however, averaged over 5 or 6 measurements, the inventive system was found to be approximately 30 times more sensitive than passive FTIR where the source used in the inventive method had a temperature of about 80° C. higher than ambient. Specifically, for these scenarios, described in greater detail in the Examples, the inventive method had a minimum detection limit of about 79 ppmV, whereas the passive method had an average minimum detection limit of 2300 ppmV. The direct comparison of the three techniques can be seen in the spectra themselves. As discussed further below, FIGS. 10-12 present the spectra measured for active, passive (i.e., sky), and inventive systems. The background spectra 704, 706, 708 were all measured with the CO flow turned off, and the corresponding spectra 705, 707, 709 are the data obtained with CO gas flowing. In the passive measurement, the gas plume is hotter than the background, so the peaks are upward-going. For the active and inventive methods, the CO peaks are seen in absorption mode.

For cases where there is no temperature difference between the plume and ambient temperature, the inventive method is infinitely better than the passive technique because the engineered temperature difference creates the measurement sensitivity. For passive measurements, in general, to observe such a species in emission mode at these (5 to 20 μm) wavelengths would require the gas to be extremely hot, perhaps tens of degrees Kelvin above ambient temperatures, depending on spectrometer sensitivity. For civilian defense purposes, such as the release of pollutant, toxic industrial material (TIM), or agent gas in an enclosed structure, where the release species are more likely to be released near room temperature, the passive technique would not provide an acceptable degree of sensitivity. In contrast, the inventive method produces a large, fixed temperature difference, resulting in tens to hundreds of times better sensitivity, especially for gas plumes near ambient temperatures. Due to their low heat capacity, gas plumes thermalize surprisingly quickly. Moreover, alignment is simplified in an inventive system due to the large infrared signal generated by the source. The detecting spectrometer or radiometer simply has to be aimed at the source, and it is easy to optimize Fourier Transform Spectrometers on a real-time interferogram. The interferogram in the inventive technique was found to be 2 to 3 times larger than when the telescope was pointed off-target, i.e., away from the source.

A person of ordinary skill in the art will readily appreciate that use of the present invention results in significant simplification of software needs as compared to a passive FTIR system, which must account for both emission and absorption features depending on the relative plume temperature. The passive IR software must thus analyze for either of two entirely different types of features. In contrast, because the inventive technique creates a significant temperature difference between the background and the intervening gas, the spectral features are almost always in absorbance, and standard spectral analysis (using the Beer-Lambert law) is enabled. This not only greatly simplifies the detection algorithm, but also greatly reduces the processing time needed to compare a test spectrum to reference spectra in an associated data library.

Moreover, the constant large radiative field removes the requirement for a high dynamic range required in a passive system. Specifically, the detector can be better configured to handle more constant light levels since the broadband source used in accordance with the invention can be maintained at a constant temperature, i.e., spectral brightness. An inventive system with a very hot source (i.e., a source that has a temperature of at least about 20° C. above room temperature) could perhaps make use of room-temperature detectors such as deuterated tryglycine sulfate (DTGS).

Another advantage of an inventive system over a passive detection system is that the heating component in an inventive system can be configured to heat the surface to a temperature at which the surface emits sufficient infrared radiation in the MWIR region of from about 1850 to about 2300 $cm^{-1}$ to produce a detectable signal in the MWIR region when a gaseous compound that absorbs radiation in the MWFR region is present. The emission of radiation in this region is a significant advantage of an inventive system compared to a passive system, wherein very little radiation in this region is available for detection. As discussed in the Examples below, in the inventive system tested, there was significantly more IR intensity in this region compared to a passive measurement, which corresponds to a vastly reduced acquisition time for the same signal/noise ratio. This region of a typical atmospheric IR spectrum is relatively free of interferants and can provide much useful information for environmental monitoring of pollutant compounds. There are several highly toxic compounds that can be monitored with far better sensitivity in the MWIR regions since they have few or no absorption bands in the long-wave IR. In addition, several common small-molecule toxins have their strongest signatures in this region. Many of these species can be monitored only poorly at LWIR wavelengths, and most not at all. They simply would not be detected in the LWIR because they have no signature in that region.

In comparison to an active technique, there is no need in an inventive system for sender telescopes or retroreflectors, each of which can cost on the order of USD 10,000. In contrast, excellent results were obtained using an inventive system in which a modified commercial pancake griddle, at a cost of about USD 40, was used as the source. Logistically, it is infinitely easier for the detection FTIR system to align on the griddle source than bore-sighting the two telescopes coaxially. In practice, the two telescopes in an active system can only be aligned by skilled operators, typically with two people in radio communication, and only with investment of a significant amount of time. For the inventive technique, alignment is especially facile since it removes the criterion for co-axial positioning, thus requiring only the less stringent angular pointing. Once a coarse alignment has been accomplished, steering optics can easily be adjusted so as to maximize the interferogram in real time. Such a mechanism can also easily employ a servo-feedback loop to optimize angular alignment. The inventive technique is robust, of minimal maintenance and several paths can be monitored adding additional (inexpensive) sources thus enabling detection of inhomogeneously distributed gas plumes. The inventive system therefore offers important operational advantages for fence line monitoring, perimeter scanning or the like. The inventive technique has successfully been demonstrated as a remote-sensing technique that is less cumbersome than active infrared sensing, yet far more sensitive than passive infrared sensing.

Reference will now be made to specific examples illustrating various preferred embodiments of the invention as described herein. It is to be understood, however, that the examples are provided to illustrate preferred embodiments and that no limitation to the scope of the invention is intended thereby.

EXAMPLES

Comparison of Inventive Remote Detection Technique to Active and Passive Detection Systems A goal of the experimental work described herein was careful quantification, under well-controlled plume release conditions, as to the relative sensitivity of the active, passive, and inventive IR detection techniques. This work was done in an open field release under adverse scintillation conditions (ambient temperature >30° C., heavy daytime turbulence), and therefore represents realistic upper bounds on sensitivity.

EXPERIMENTAL CONSTRUCT

Measurement Layout

Figure 6:
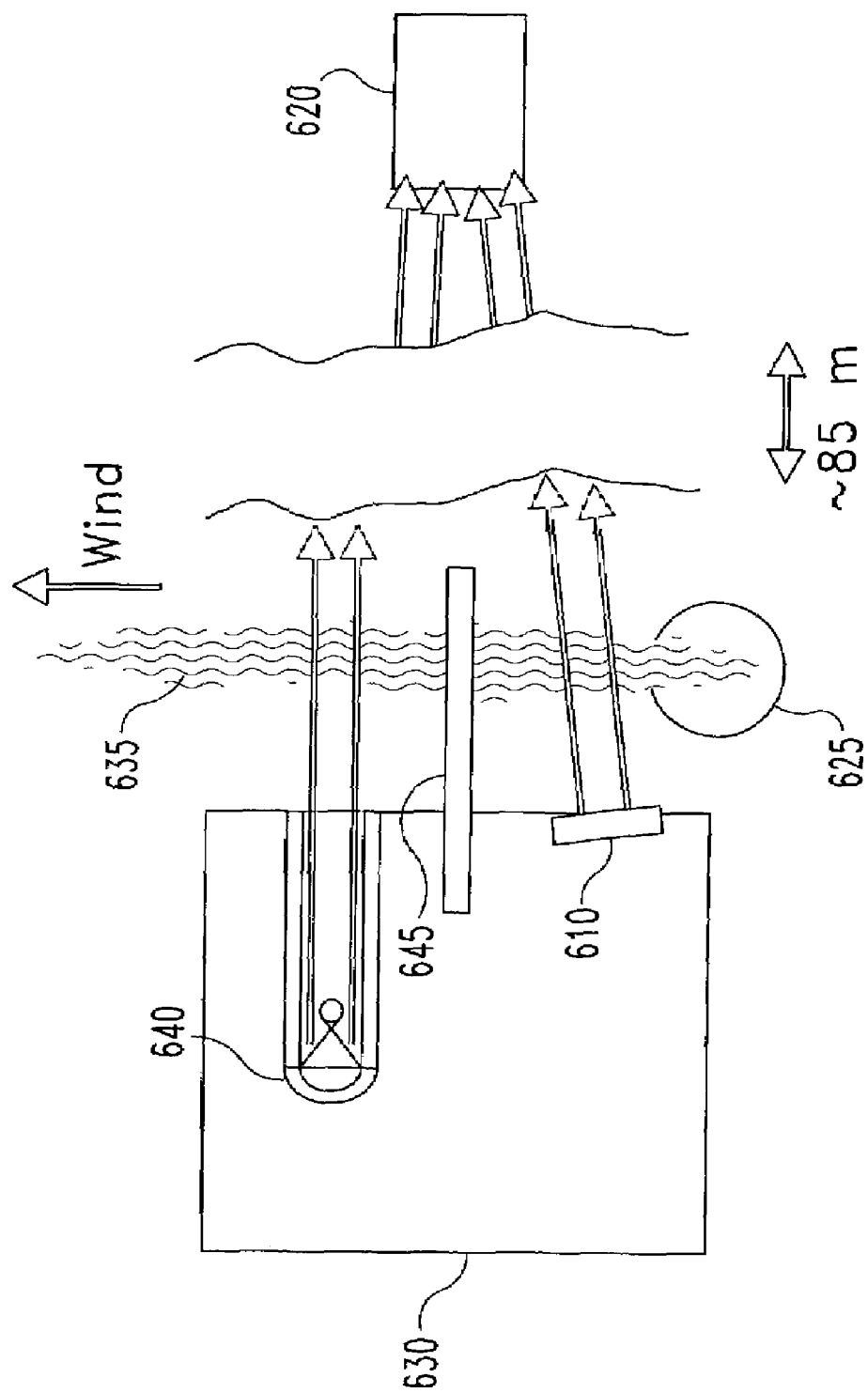
FIG. 6 is a schematic plan view diagram of a measurement configuration used to compare passive, active, and inventive measurements as described in the Examples.
Figure 7:
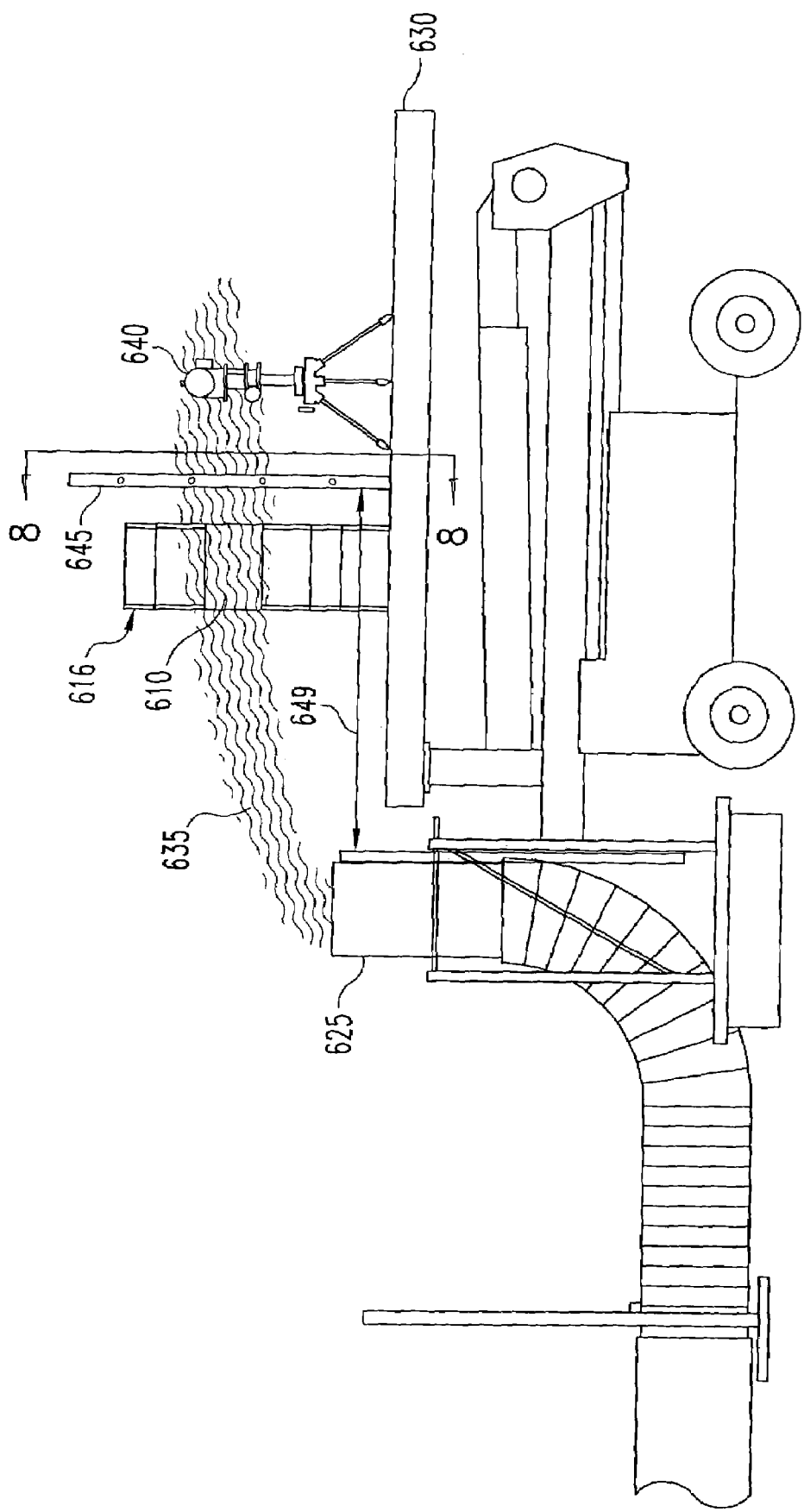
FIG. 7 depicts a typical plume trajectory when the manlift was positioned 209.5 cm (82.5 in.) downwind from the release stack, as described in the Examples.

These experiments were carried out using a constructed "short stack," which was approximately 3 meters (10 feet) tall, for releasing a gas plume, with a mobile manlift platform positioned nearby to support certain equipment as described herein. A schematic layout of the top view of the experiment is shown in FIG. 6, and a schematic side view is shown in FIG. 7. Immediately downwind from the short stack 625, a mobile manlift platform 630 was placed adjacent to the approximate plume path 635. The manlift supported a sender telescope, the heated griddle, and a thermocouple array.

For detection, receiver 620 included a MIDAC 2401 C FTIR emission spectrometer coupled to a 35-cm Newtonian telescope that gathered the IR light and re-collimated it into a 3.8-cm diameter collimated beam. The light was reflected into the spectrometer through a ZnSe window and intensity modulated by an interferometer using a Ge/ZnSe beamsplitter. The linear motion interferometer modulated the IR light, and the beam was focused onto an Infrared Associates 16-0.5 mercury cadmium telluride (MCT) 0.5×0.5 mm detector operating at 77 K. The spectrometer and detection system were set atop a steel platform for mechanical stability. The communications link at the site allowed data acquisition to be synchronized to the releases from the 10-foot short stack. Light in both the MWIR (3 to 5 μm) and LWIR (7 to 14 μm) atmospheric windows was of interest; a short-pass filter was used to filter out ficht of wavelengths shorter than 2.5 μm, allowing increased electronic gain to avoid some of the "bit noise" associated with the 16-bit 100 kHz analog-to-digital converter (ADC). The MCT 0.5×0.5 mm detector element, coupled with the spectrometer's field-of-view as further magnified by the telescope produced a theoretical field-of-view of approximately 1.1 mrad. The theoretical image size at 100 meters would thus be 0.11 meters (11 cm), but distortions due to imperfect optics and scintillation are significant, and a more realistic image size at this distance is estimated as 0.15 meters.

The spectrometer has an ultimate (unapodized) spectral resolution of 0.5 $cm^{-1}$, and for the passive/active/inventive comparison studies discussed herein for carbon monoxide (CO), the spectral resolution was set at 1.0 $cm^{-1}$ due to the narrow spectral linewidths. The interferograms were triangular-apodized, zerofilled a factor of four and transformed using the Cooley-Tukey algorithm. The software controlling the spectrometer and used for data evaluation was Grams 32 Version 4.11. For band integration and relative temperature characterization, the data were analyzed using Bruker's OPUS-NT software, Version 3.0. Other parameters are consistent with the FTIR parameter settings outlined by Bertie JE. 1998. "Specification of Components, Methods and Parameters in Fourier Transform Spectroscopy by Michelson and Related Interferometers," *Pure and Appl. Chem.* 70(10):2039-2045.

The release gases used for these studies were selected as $SF_6$ and CO. The release flow rates for carbon monoxide for the various segments are compiled in Table 1, infra. $SF_6$ was used as a "known" to help in alignment due to its especially large absorption cross-section. Because CO has only a moderate IR cross-section (as reported in the literature: band strength=$1.027 \times 10^{31}$ $^{17}$ cm/molecule=276 $cm^{-2}$ $atm^{-1}$ at 273.15 K), and because the present spectrometer has only moderate sensitivity, large concentrations of CO (2,500 to 10,000 ppmv) were provided for these segments. CO was also selected because its resolved ro-vibronic lines allow for an internal calculation of the plume temperature. Another motivation in selecting CO is to demonstrate the detectability of a species that would be effectively "invisible" in most passive IR systems, since they predominantly utilize the LWIR window between 7 and 14 μm. Carbon monoxide's fundamental vibrational mode lies in the MWIR at about 4.5 μm (2143 $cm^{-1}$). This extended wavelength capability is further discussed below.

All IR data were analyzed using reference spectra from the PNNL Northwest Infrared database. These data are of high precision and accuracy both on the wavelength and intensity axes. Each 25° C. spectrum in the database is in fact a composite spectrum derived from a Beer's law fit to 10 or more individual measurements, each at a different burden. The database protocol has removed several artifacts associated with FTIR measurements for real-time remote sensing (Johnson T J, R L Sams, T A Blake, S W Sharpe, and P M Chu. 2002. "Removing Aperture-induced Artifacts from Fourier Transform Infrared Intensity Values," *Appl. Optics,* 41:2831-2839.). The database has been further vetted against the National Institute for Standards and Technology (NIST) quantitative infrared database (Chu P M, F R Guenther, G C Rhoderick, and W J Lafferty. 1999. "The NIST Quantitative Infrared Database," *J. Res. Natl. Inst. Stand. Technol.* 104:59-81.). The two databases have been found to agree (measured across the entire spectrum) to approximately one percent, which is well within the cumulative experimental error of 2.2 percent (Johnson et al. 2002). The focus of the present study, however, is to investigate the possibility of using a new inventive method for accurate and sensitive detection.

Extended Broadband Source

Based on the discussion above, a source was desired that could fill the field-of-view (FOV) of the spectrometer at a distance of approximately 100 meters and maintain a substantially uniform temperature across the face of the source at least about 80° C. higher than ambient background. Thus, in a system in which the source and receiver are separated by about 100 meters, it was determined that the source should have a surface of approximately 15 cm diameter in order to fill the FOV of the present spectrometer/telescope, should be capable of maintaining an absolute temperature requirement of about 110° C., (about 230° F.), and should have a relatively high emissivity. A commercial "pancake griddle" was identified as being a suitable source upon consideration of these requirements. Thus, rather than construct a custom source, a commercial pancake griddle was used, represented schematically in FIGS. 6 and 7 as griddle 610. The griddle is designed for continuous 110° C. operation, and has a face with a high emissivity (low reflectivity), thus approximating a nearly ideal blackbody source. The griddle was modified to act as a source for this experiment in only three ways. First, the griddle was installed on a vertical mount with a bright frame so as to quickly attach to the manlift. The bright frame 216 allowed it to be readily sighted at large distances. In addition, the thermostat circuitry was replaced by a simple "variac" voltage regulator to provide a constant voltage to the device. Third, four different thermocouple temperature sensors were affixed to the griddle in random locations to gauge the average griddle temperature as seen by the spectrometer. The four sensors' temperature data (along with the thermocouple data) were read out and stored approximately every 1.5 seconds throughout the afternoon. The griddle temperatures reported here are a simple mean calculated from the four sensors. In fact, each of the four sensors reported a fairly constant temperature over the several minutes of the IR measurement, but the four temperatures were quite different from each other. For example, during the 3-minute measurement period corresponding to measurement GR10 (13:48-13:50), the four griddle temperatures reported were 93.9±3.3, 105.9±2.3, 125.5±2.1, and 125.4±1.5° C. The difference in the four temperatures reflects the relative inhomogeneity across the radiating surface due to the relative proximity of the sensors to the actual heating elements. A typical mean griddle temperature during the course of the afternoon was 110° C. During the afternoon of the testing, the air temperature was about 32.5° C., the griddle thus creating a temperature difference to ambient of about 80 K.

Besides prototyping the inventive method, an additional objective of the experiment was to facilitate as direct a comparison as possible between the passive, active, and inventive techniques. Thus, three IR sources were situated adjacent to one another on the manlift platform 630: the active source 640, i.e., sender telescope, the "griddle" broadband source 610 used in connection with the inventive technique, and the ambient sky in between (i.e., for passive FTIR). The active sender was an air-cooled SiC glow bar from Bruker mounted at the focal point of a 15-cm Newtonian telescope. The griddle has been described. For the passive FTIR, the focal point was just above the horizon between the two above-mentioned sources. During each measurement, the detector telescope was aimed at the sender telescope, the griddle source, or the sky, in succession. On the receiver, a simple alignment "rifle" telescope was used to attain coarse alignment. For fine alignment, the interferogram centerburst was used to optimize the alignment signal on the active and inventive sources. The FTIR spectrometer was located at a crosswind distance of 89.2 meters from the stack, approximately 90 meters from the manlift and the sources.

Figure 8:
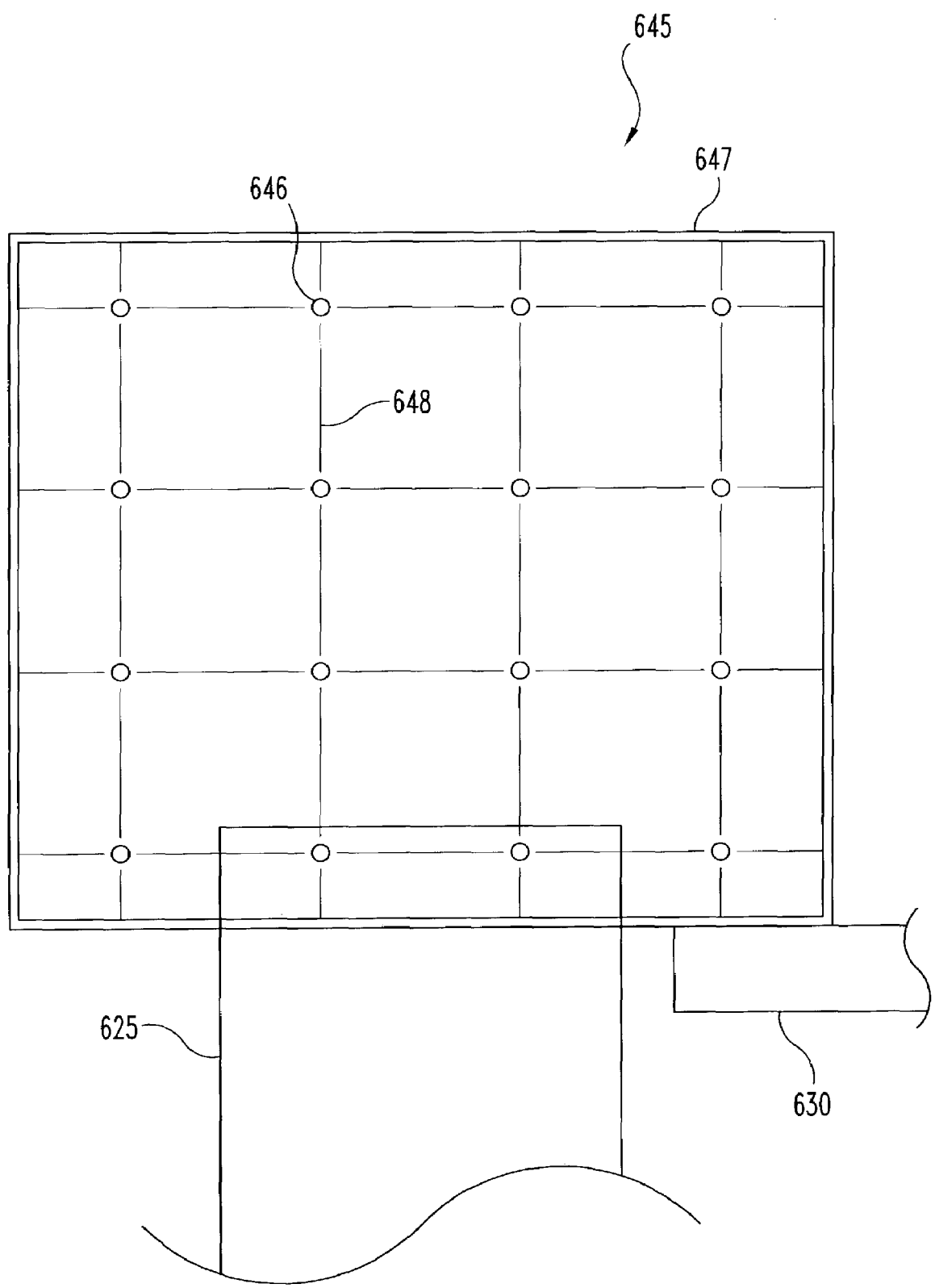
FIG. 8 is a schematic diagram of a thermocouple array as described in the Examples.

A second experiment was being run in parallel to investigate the rate of plume thermalization under real-world ambient conditions; these plume thermalization experiments dictated the approximate positions of the manlift. The plume thermalization experiment was designed to measure the plume temperature at a series of different positions downwind from the stack to experimentally determine how quickly the plume cools due to mixing and radiative cooling. In fact, plume cooling was observed to be quite rapid as the manlift was repositioned downstream. The experimental construct, depicted schematically in FIG. 8, consisted of an array 645 of sixteen thermocouple sensors 646 formed into a 4×4 grid pattern on 30 cm (1 ft) centers. The thermocouples were mounted to the grid frame 647 using thin wires 648 so as to sense the plume temperature in situ without significantly obstructing the plume flow. Using this thermocouple grid as the plume temperature sensor, the manlift was therefore positioned at three different downwind positions during the course of the afternoon to measure plume cooling: 50.8 cm, 97.8 cm, and 209.5 cm (from the metal edge of the stack to the thermocouple array—see arrow 649 in FIG. 7). Note that the plume traversed in front of both the griddle and sender telescope, and is centered near the third row of thermocouples. The arrow indicates the length used to measure the downwind distance of the stack edge to the thermocouple array, which was varied by moving the manlift. A total of 39 measurements were made.

The measurements were broken into series, corresponding to the three different positions of the manlift downwind from the stack, with different sources being observed and different gas concentrations being released at each position. At each of the manlift positions, 12 IR measurements were made: With the gas flows turned off, background measurements were recorded for each of the three techniques, namely 1) passive (detector telescope aimed at open sky), 2) active (detector telescope aimed at sender telescope), and 3) inventive (telescope pointed at the griddle). The release sequences are compiled in Table 1.

For the actual chemical measurements, the same sequence was repeated after the gases had been activated and flows stabilized. At each manlift position, nominal CO mixing ratios of 10,000, 5,000, and 2,500 ppmV were used. At the last manlift position, an additional measurement was made as the stack cooled to near ambient temperature. To achieve this, the blowers were left on, but the jet start carts (the source of heated air) were turned off. This produced a release temperature near 60° C. at the top of the stack, as opposed to the 130 to 140° C. stack release temperature achieved using the full flow that included the start carts. Table I also reports the stack gas (release) temperatures as recorded by a single thermocouple located about 25 cm (about 10 in.) below the inside rim of the short stack, while the plume was still hot. As the thermocouple data showed, the rate of cooling of this plume was very rapid, dropping tens of degrees Celsius within one or two meters of the release.

EXPERIMENTAL RESULTS

Spectral Results

Figure 9:
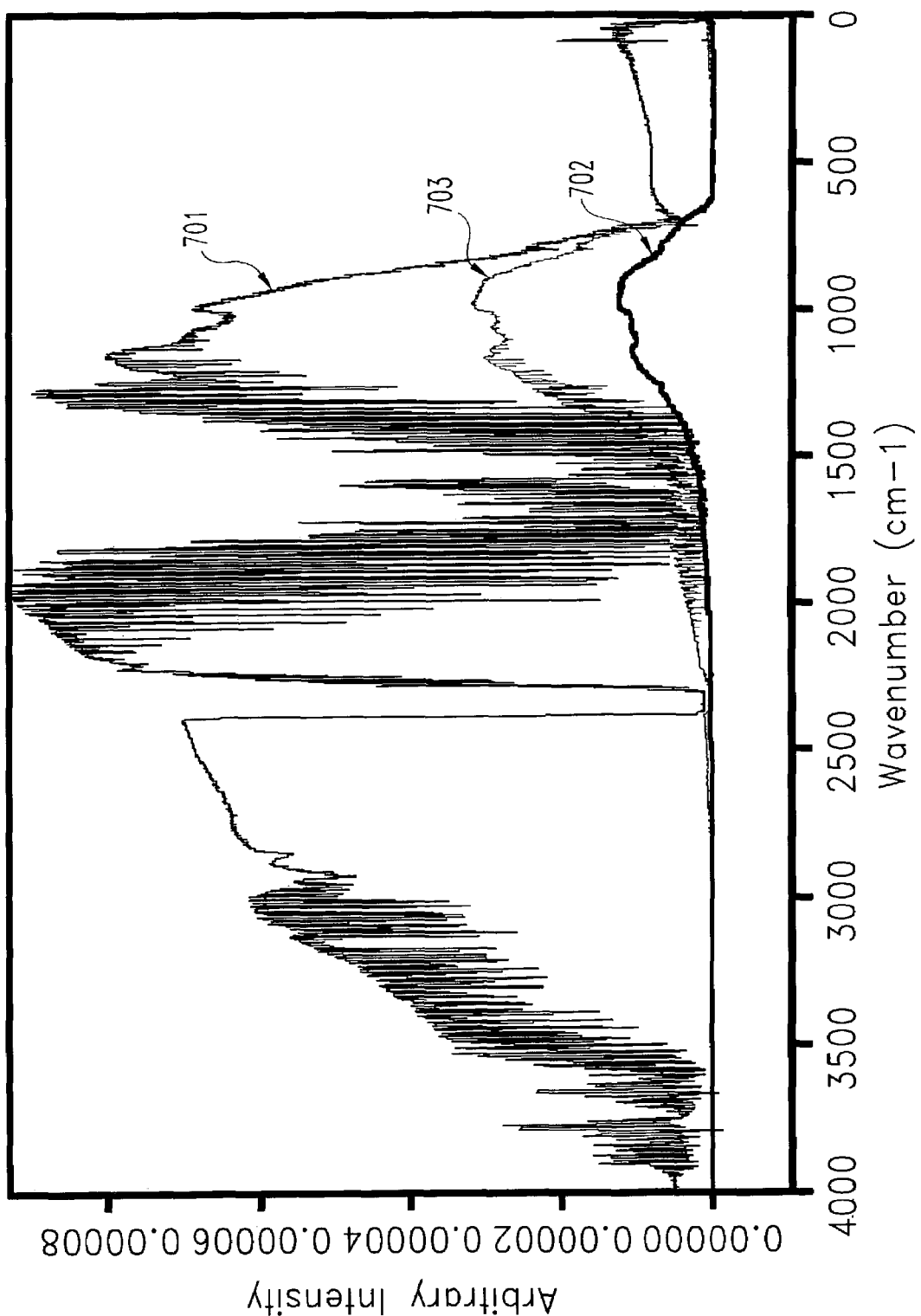
FIG. 9 depicts the intensity of the IR signal measured using three different techniques, as described in the Examples. Each of the three spectra is a "background" spectrum, i.e., with no analyte gas flowing from the stack. Trace 701 corresponds to the active measurement, trace 702 to a purely passive technique, and trace 703 to an inventive technique.

Single-beam reference spectra from each of the three techniques are shown in FIG. 9, where the IR signal intensity

TABLE 1

Experimental Parameters and Acquisition Sequence

| File | Time Intv'l | Site | Release Mixing Ratio/CO | Grid-Stack (cm) | Stack Temp+ (° C.) | Plume Temp# (° C.) | Griddle Temp (° C.) | Bkgd Temp (° C.) |
|---|---|---|---|---|---|---|---|---|
| GR10 | 1348–50 | Griddle | 0: Bkgrnd | 50.8 | 130 | 68.1 | 112 ± 13 | 32.8 |
| SK10 | 1352–54 | Sky | 0: Bkgrnd | 50.8 | 130 | 71.1 | | 32.9 |
| TL11 | 1406–08 | Sender | 0: Bkgrnd | 50.8 | 133 | 66.2 | | 32.7 |
| TL12 | 1419–21 | Sender | 10,000 ppm | 50.8 | 133 | 70.2 | | 33.8 |
| GR12 | 1423–25 | Griddle | 10,000 ppm | 50.8 | 133 | 72.7 | 97 ± 12 | 33.7 |
| SK12 | 1426–28 | Sky | 10,000 ppm | 50.8 | 133 | 73.4 | | 33.4 |
| TL13 | 1431–31 | Sender | 5,000 ppm | 50.8 | 133 | 72.6 | | 33.8 |
| GR13 | 1434–36 | Griddle | 5,000 ppm | 50.8 | 133 | 66.9 | 97 ± 13 | 33.8 |
| SK13 | 1436–38 | Sky | 5,000 ppm | 50.8 | 133 | 73.4 | | 33.3 |
| TL14 | 1439–41 | Sender | 2,500 ppm | 50.8 | 133 | 68.5 | | 33.7 |
| GR14 | 1442–44 | Griddle | 2,500 ppm | 50.8 | 135 | 71.3 | 97 ± 12 | 33.2 |
| SK14 | 1444–46 | Sky | 2,500 ppm | 50.8 | 135 | 67.4 | | 33.0 |
| TL15 | 1530–32 | Sender | 0: Bkgrnd | 97.8 | 133 | 62.8 | | 32.9 |
| GR15 | 1534–36 | Griddle | 0: Bkgrnd | 97.8 | 133 | 59.3 | 109 ± 13 | 33.5 |
| SK15 | 1538–40 | Sky | 0: Bkgrnd | 97.8 | 140 | 61.2 | | 33.1 |
| TL16 | 1547–49 | Sender | 10,000 ppm | 97.8 | 139 | 60.0 | | 33.6 |
| GR16 | 1550–50 | Griddle | 10,000 ppm | 97.8 | 139 | 61.0 | 107 ± 13 | 33.5 |
| SK16 | 1553–55 | Sky | 10,000 ppm | 97.8 | 140 | 62.0 | | 33.3 |
| TL17 | 1556–58 | Sender | 5,000 ppm | 97.8 | 141 | 58.6 | | 33.1 |
| GR17 | 1559–01 | Griddle | 5,000 ppm | 97.8 | 142 | 59.5 | 109 ± 14 | 33.6 |
| SK17 | 1601–03 | Sky | 5,000 ppm | 97.8 | 142 | 61.6 | | 33.8 |
| TL18 | 1610–12 | Sender | 2,500 ppm | 97.8 | 138 | 61.3 | | 33.5 |
| GR18 | 1613–15 | Griddle | 2,500 ppm | 97.8 | 138 | 51.1 | 102 ± 14 | 33.5 |
| SK18 | 1636–38 | Sky | 2,500 ppm | 97.8 | 135 | 61.0 | | 33.3 |
| TL19 | 1707–09 | Sender | 0: Bkgrnd | 209.5 | 120 | 49.1 | | 33.3 |
| GR19 | 1714–16 | Griddle | 0: Bkgrnd | 209.5 | 137 | 50.3 | 106 ± 12 | 33.5 |
| SK19 | 1717–19 | Sky | 0: Bkgrnd | 209.5 | 137 | 49.9 | | 33.4 |
| TL20 | 1723–25 | Sender | 10,000 ppm | 205.5 | 139 | 49.9 | | 33.3 |
| GR20 | 1726–28 | Griddle | 10,000 ppm | 209.5 | 139 | 49.5 | 106 ± 13 | 33.2 |
| SK20 | 1728–30 | Sky | 10,000 ppm | 209.5 | 140 | 50.0 | | 33.3 |
| TL21 | 1732–34 | Sender | 5,000 ppm | 209.5 | 134 | 51.1 | | 33.0 |
| GR21 | 1735–37 | Griddle | 5,000 ppm | 209.5 | 140 | 51.4 | 105 ± 11 | 33.0 |
| SK21 | 1737–39 | Sky | 5,000 ppm | 209.5 | 140 | 52.0 | | 33.2 |
| TL22 | 1741–43 | Sender | 2,500 ppm | 209.5 | 142 | 49.9 | | 33.2 |
| GR22 | 1745–47 | Griddle | 2,500 ppm | 209.5 | 142 | 49.9 | 96 ± 12 | 33.0 |
| SK22 | 1478–50 | Sky | 2,500 ppm | 209.5 | 142 | 51.9 | | 33.1 |
| TL23 | 1800–02 | Sender | 5,000 ppm | 209.5 | *71 | 40.7 | | 32.4 |
| GR23 | 1802–04 | Griddle | 5,000 ppm | 209.5 | *66 | 40.6 | 103 ± 13 | 32.4 |
| SK23 | 1804–06 | Sky | 5,000 ppm | 209.5 | *63 | 40.8 | | 32.4 |

+Stack Temp Sensor 10 in. below rim.
Temps from thermocouple grid.
*Start cart off, only blowers on has not been calibrated into radiance (W/m$^2$ sr cm$^{-1}$), but is on the same constant signal scale for the three different techniques. The three traces 701, 702, 703 correspond to the active method (sender), the passive method (sky), and the inventive method (griddle), respectively. The relative amplitude of the signals is notable, since the y-axis is the same for all measurements. The apparent amplitude below 700 cm$^{-1}$, is an artifact due to the MCT detector nonlinearity; the artifact is especially flagrant at the high light levels of the active measurement. The measurements were made in direct succession, e.g. TL19, GR19, and SK19.

As can be seen in FIG. 9, the active technique (trace 701) clearly provides the greatest IR amplitude and hence the greatest sensitivity. But in fact, it is the amplitude difference (also called the spectral contrast) between the background and the sample signals that determines both the sensitivity and thus the specificity. We see that species such as CO (absorbing in the MWIR at wavenumbers greater than 1800 cm$^{-1}$) would be extremely difficult to measure with passive IR spectroscopy in absorbance mode due to the lack of IR light at these wavelengths (note the virtual absence of signal at frequencies greater than 1500 cm$^{-1}$ in trace 702). In absorption mode, the ambient signal is even less than the reference IR signal, and this creates a scenario of subtracting two small numbers from one another, which results in large errors. To observe such a species in emission mode at these wavelengths would require the gas to be rather hot, perhaps tens of degrees Kelvin above ambient temperatures, or even more depending on the spectrometer's noise floor, often called the noise-equivalent delta-Temperature (NE$\Delta$T).

FIGS. 10-12 plot portions of the "sample" and "background" spectra for the three different techniques from single beam spectra. FIG. 10 represents spectra obtained using the active technique; FIG. 11 represents spectra obtained using the inventive technique; and FIG. 12 represents spectra obtained using the passive technique. Traces 704, 706 and 708 are background spectra and traces 705, 707 and 709 are sample spectra. Although the x-domain is the same in all three, the y-axes are on very different scales. In each case, the background spectrum is recorded under identical conditions, save the absence of the chemical in the plume. In regards to FIG. 12, we note there are several methods available to extract chemical identity information using passive IR spectroscopy. The direct method simply involves subtracting the "off-plume" from the "on-plume" spectrum. An alternative method that has been proposed involves subtracting a blackbody spectrum at the same temperature as the plume to increase sensitivity. Yet another alternative method "pattern matches" the interferogram (rather than the spectrum) with the corresponding interferogram of the analytes of interest. Only that portion of the interferogram is used with the strongest signatures for the analytes of interest. This method can seek out the most information-laden portion of the interferogram, and also avoids the (computationally slow and intensive) Fourier transform, which can be very advantageous, especially since the FT can be slow at high spectral resolution.

As opposed to the passive technique, in both active IR and in the system of the present invention, there is sufficient spectral contrast between the sample and background spectra such that the data can be processed as absorption spectra $A=-\log(I/I_o)=\epsilon dC$ using the background or a synthetic line as the reference spectrum. This further simplifies the analysis as compared to the passive case where the evaluation software must account for both absorption- and emission-type features, depending on the relative temperatures. Following Kirchhoff's Law in the limit that the background and plume have the same emissivities, then no radiance difference will be observed when the plume and background achieve equal temperature. The traces shown in FIGS. 10-12 emphasize this for the case when $\epsilon_B \approx \epsilon_{PLUME} \sim 1$ (optically thick region), since the temperature difference governs the size of the signal.

Verification of Plume Path

The relative IR amplitude of the blackbody radiance spectra seen, for example, in FIG. 9 indicates that the spectrometer was correctly focused on the appropriate sources. During the experiment, however, additional methods were used to verify to a reasonable degree of confidence that the same concentration-time product of the CO plume was in the FOV during each of the measurement scenarios (about 2.5 minutes each). For each of the reported segments, the flow and mass measurement wind-velocity and wind-speed data clearly show that, on average, the plume followed a dispersion pattern similar to that rendered in FIG. 7, which shows a diagram of the manlift and associated hardware when the manlift was positioned 210 cm downwind from the edge of the stack. The plume is sketched as primarily traversing between the second and third thermocouple rows from the bottom, with a greater weight toward the third row, which is typical of what the meteorological data indicated. More definitively, the plume and thermocouple grid array data also show, by interpolating to the points of highest temperature, that the plume followed trajectories similar to that shown in FIG. 7. The spectra themselves show the presence of carbon monoxide at relatively constant concentrations, so long as there were no major changes in wind velocity/direction. As such, we may approximate the average CO mixing ratio in the plume as relatively constant at some value less than the release value at the release point at the top of the stack (e.g. 2500 ppmV), and further that the plume path as shown in FIG. 7 is a reasonable approximation to the average plume path during the data acquisition periods (about 2.5 minutes each). To be sure, turbulent wind patterns will dilute and disperse the plume more than that expected for simple Gaussian diffusion during any one measurement. This dilution is further discussed below.

The TC data further indicate that the plume cools rapidly, presumably due to turbulent mixing. This mixing would in turn mean that the CO concentrations have also significantly dropped, even though the plume is not far from the stack. As expected, during periods of higher wind velocity (5 to 8 m/s), the plume "kneeled over," traversing the lower sensors in the thermocouple grid and thus being slightly below the griddle for certain measurements. At lower average wind velocities, typically 2 to 4 m/s, the plume was closer to the top of equipment mounted on the manlift. The most important point in terms of the inventive technique is that on average a good portion of the plume traversed the IR sensor's field-of-view. The only exceptions to this were for the early-afternoon measurements when the TC grid was positioned only 50 cm downwind from the stack. In these segments (11 through 14) the wind was strong enough and the manlift close enough that the plume had its hottest, densest point in either the first or second row of the TC grid, primarily the first (lowest) row. As a consequence, little of the plume concentration traversed in front of either the griddle or the sender telescope, as was further verified by the very weak CO absorption signal. This was especially true for the GR18 sequence, where essentially no CO was detected.

Sensitivity and Linearity Analysis

With reference to FIG. 9, the most straightforward data to evaluate are those of the active measurements. For these measurements the plume temperature is clearly much lower than that of the sender telescope source, so Beer's law can be used to calculate a concentration-path-length product. The absorbance values are calculated by using $-\log(I/I_o)$ where the $I_o$ spectrum was obtained accordingly as TL15 or TL19 with no analyte gas flowing.

The nominal stack release concentrations in these experiments were 10,000, 5,000, and 2,500 ppmV, respectively. We observe the linear behavior between the recorded absorbance and the approximate mixing ratio of the release gas. Although the concentrations are very high, the nearly linear behavior and excellent signal/noise ratio are reassuring. In fact, the ratios of the CO band integrals (2230 to 2043 cm$^{-1}$) for the three measurements fall in the ratio 2.50:4.65:9.07 (lowest to highest, compare 2.5:5:10). The fact that the ratio declines systematically may also indicate multiple scattering effects, e.g. IR re-emission from optically dense plumes; such effects can lead to an underestimate when optical depths are $\geq 1$. These data have not been smoothed or manipulated in any fashion, only vertically offset for clarity.

To compare the sensitivity of the three different methods, it is useful to gauge the magnitude of the absorption signal. In a passive remote sensing experiment, the only value that can be absolutely determined is the product of (concentration)×(path length)×(temperature difference) [in units of ppm-m-K] as discussed above. However, we know the plume temperature because of the thermocouple array data; it has also been determined from the CO absorption-band profile. It is possible to further evaluate the data at hand because the plume temperature in this experiment is much lower than that of the sender telescope used in the active measurement, and we thus calculate using Beer's law to yield a concentration-pathlength product. The mixing ratio of the plume upon exiting the stack is also known; the only unknown quantities are the exact path length (i.e., the plume diameter) and the dilution factor. As a first approximation, we take the plume cross-section as a circle. From the thermocouple grid array measurements, it can be estimated as a Gaussian distribution within a circle of approximately 0.3 meters (1 foot) in diameter. We can thus use the active IR measurements to calculate a plume mixing ratio, which must clearly be less than the stack-release concentration (either 2,500 or 5,000 or 10,000 ppmV for these calculations). The results of these concentration estimates are presented in Table 2, Column 6. An additional important observation is that at 1 cm$^{-1}$ resolution, the lines of CO are not fully resolved at atmospheric pressure. This poses a linearity problem since it was subsequently determined that some of the stronger CO lines were optically saturated. Hence, we must treat the CO mixing ratios for the 10,000-ppmV segments with some suspicion because of the saturation/nonlinearity of the stronger lines. For both the active and inventive measurements, the measured integrated band strengths of CO are listed in Table 2. The integration limits were chosen as 2230 to 2043 cm$^{-1}$ to include the strongest CO lines; spectra were baseline corrected before integration.

TABLE 2

Sensitivity Estimates for CO for Active, Passive, and Inventive Remote Sensing. Note that for Segment 18 the strong winds pushed the plume below the FOV for most segments.

| File-Target | Stack/Bkgd temps (° C.) | Stack Mixing Ratio CO (ppm) | Peak HT:CO 2179 cm$^{-1}$ | ∫CO Band (cm$^{-1}$) | Est. CO Mixing Ratio (ppm) (assume 0.3 m) | Calc. Detect Limit (ppm) |
|---|---|---|---|---|---|---|
| 97.8 cm | | | | | | |
| TL16-Sender | 139/33.6 | 10,000 | 0.2164 | 6.2781 | 1,950 | 3.66 |
| GR16-Griddle | 139/33.5 | 10,000 | 0.1941 | 5.8439 | 1,815 | 95 |
| SK16-Sky | 140/33.3 | 10,000 | | | | 1856 |
| TL17-Sender | 141/33.1 | 5,000 | 0.2012 | 6.0129 | 1,867 | 2.05 |
| GR17-Griddle | 142/33.6 | 5,000 | 0.1589 | 4.7400 | 1,472 | 118 |
| SK17-Sky | 142/33.8 | 5,000 | | | | 1054 |
| TL18-Sender | 138/33.5 | 2,500 | 0.1038 | 3.0230 | 939 | 4.29 |
| GR18-Griddle | 138/33.5 | 2,500 | 0.0202 | 0.6462 | 201 | xxx |
| SK18-Sky | 135/33.3 | 2,500 | | | | 676 |
| 209.5 cm | | | | | | |
| TL20-Sender | 139/33.3 | 10,000 | 0.2211 | 6.4961 | 2,018 | 2.89 |
| GR20-Griddle | 139/33.2 | 10,000 | 0.1883 | 4.2280 | 1,313 | 86 |
| SK20-Sky | 140/33.3 | 10,000 | | | | 5092 |
| TL21-Sender | 134/33.0 | 5,000 | 0.1256 | 3.3334 | 1,036 | 2.97 |
| GR21-Griddle | 140/33.0 | 5,000 | 0.0987 | 1.8631 | 579 | 111 |
| SK21-Sky | 140/33.2 | 5,000 | | | | 4420 |
| TL22-Sender | 142/33.2 | 2,500 | 0.0762 | 1.7913 | 556 | 4.85 |
| GR22-Griddle | 142/33.0 | 2,500 | 0.0972 | 1.5883 | 493 | 88 |
| Sk22-Sky | 142/33.1 | 2,500 | | | | 804 |
| 209.5 cm, cooler* | | | | | | |
| TL23-Sender | 71/32.4 | 5,000 | 0.1710 | 4.3789 | 1,360 | 7.97 |
| GR23-Griddle | 66/32.4 | 5,000 | 0.1728 | 3.5873 | 1,114 | 160 |
| SK23-Sky | 63/32.4 | 5,000 | | | | >5000 |

*Start cart turned off; only manifold blowers on for TL23, GR23, and SK23.

In Table 2 we have calculated the concentrations (mixing ratios) for the active and semi-active measurements using the Beer-Lambert law and an assumed path length of 30 cm. The derived band integrals and corresponding mixing ratios are tabled adjacent to the signal/noise ratios. The 0.3-m path length is clearly somewhat arbitrary, but was selected because the thermocouple data suggested. a hottest plume cross-section that had dropped markedly in temperature at any adjacent thermocouple sensor (the sensors were placed at 0.3 meter [1-foot] centers). Moreover, a separate video using an infrared camera also showed that for flow near the manlift, the visible part of the plume was typically about 0.3 meters (about 1 foot) across. Clearly this is an estimate, and if, for example, we estimate the path length as 0.6 meters, the mixing ratios listed in the sixth column would all be halved. In any case, the calculated mixing ratio has been derived by integrating the 2230 to 2043 cm$^{-1}$ region, assuming a 0.3-meter path and then dividing the results by the same integral obtained from the NWIR database reference data. For the inventive measurements the signal and noise levels were calculated in exactly the same manner as for the active measurements. To be sure, the temperature difference is not as large as with the active method, but the griddle creates a spectral contrast that allows one to use a Beer's law calculation. The analysis is simplified since it is no longer necessary to also consider the emission scenario as with passive FTIR. For the passive technique, however, the data clearly cannot be processed in the same manner. These data were treated in a manner similar to that used in actual passive IR data processing, namely the off-plume spectrum was subtracted from the on-plume spectrum, and the signature signal was sought in the difference spectrum.

The active and inventive absorption data were analyzed for signal strength by calculating the peak height of the R (9) CO absorption at 2179.8 cm$^{-1}$ (Maki G. and J S Wells. 1991. *Wavenumber Calibration Tables from Heterodyne Frequency Measurements*, NIST Special Publication 821, National Institute of Standards and Technology, U.S. Government Printing Office, Washington D.C.). The noise levels were calculated using the 2450 to 2400 cm$^{-1}$ region, which was selected so as to calculate the noise level in an adjacent spectral domain, yet avoid the effects of fluctuations in the CO, $CO_2$, or $H_2O$ concentrations. For the detection limit, the absorption peak height was divided by twice the root-mean-square (RMS) noise value from the 2450 to 2400 cm$^{-1}$ region. Although this may be a somewhat generous estimate of the actual detection limit, more rigorous analytical methods could probably elicit more from the same data set, for example, using partial-least-squares (PLS) or classical-least-squares (CLS) techniques as described in the literature. The signal/noise analysis yields a reasonable self-consistent estimate of the sensitivity.

As mentioned above, the passive data were treated in a typical manner with the off-plume spectrum subtracted from the on-plume spectrum. In a fashion analogous to the active methods, the peak height of the CO 2179.8 cm$^{-1}$ line was divided by twice the RMS noise as calculated in the 2400 to 2450 cm$^{-1}$ region. The results are also presented in Table 2. To derive an actual detection limit, however, absolute signal strength had to be assigned to the passive signals. This was done differently than for the other two techniques; namely, the stack release concentration was used as the "ground truth" value mixing value from the flow measurements, rather than the derived concentration.

The sixth column in Table 2 shows the calculated mixing ratios of carbon monoxide using an estimated path of 0.3 meters. The agreement between the active (TLxx) and inventive (GRxx) measurements is extremely good, showing that the plume path traversed both the griddle source and active source as sketched in FIG. 7, and also that the methods are consistent, i.e., the inventive technique yields approximately the same concentrations as those calculated by the more traditional active measurement. The agreement is good with the griddle values 10 to 20% less than the active values. The only set of data for which this is not true is for the GR18/TLI8 pair. Upon reviewing the meteorological data, however, this set had the strongest average winds (7.2 m/s) for the segment where the manlift was located 98 cm from the stack. In this case, the very strong winds seem to have simply directed the plume partially under the thermocouple grid (and far below the griddle altogether). This is further corroborated by all thermocouple temperatures in GR18 being approximately 5° C. cooler (and barely above ambient) than in the previous GR17 measurement. The same was found to be true for the earliest sequences at 50.8-cm downwind, where the passive and active measurements clearly saw the plume, but the griddle was located too high and too far to the left to detect much CO for the prevailing wind conditions. These data are not included in the analysis.

For the active measurements, if we disregard the xx 18 data and average the five other analogous sequences we find that the mean detection limit of the five TLxx values is 2.5 ppm, whereas for the GRxx values, the average is 79.2 ppm. As expected, the active technique is more sensitive since there are far more IR photons in the active experiment (so long as alignment is maintained). The active technique thus appears to be about 31 times more sensitive for this absorption feature for this configuration. The sender has a 1350 K source whose blackbody output maximizes near 1600 cm$^{-1}$, not far from the 2143 cm$^{-1}$ absorption of CO. The results are readily interpreted in that IR experiments are typically dominated by detector noise due to the high background radiation present at ambient temperatures Although there are many experimental variants, this provides at least a first gauge as to the relative sensitivity of the techniques.

Also important is the relative performance of the inventive technique versus passive spectroscopy, also tabulated in the 7th column of Table 2. For the passive measurements the detection limits had to be calculated using the stack release ratios of CO. However, for the same set of measurements, GR16-GR22, the passive measurement yielded an average detection limit of 2317 ppmV. Recalling that the inventive technique had a detection limit of 79.2 ppmV, this corresponds to a sensitivity of the inventive method that is 29 times better than the passive method for identical measurement conditions. Again, there is much variation in how the data are evaluated and interpreted, but this factor of approximately 30 times greater sensitivity appears to be fairly accurate. The additional greater sensitivity of the active technique over the inventive method also appears to be fairly accurate, since this in turn corresponds to about 900 times greater sensitivity of the active versus the passive method, which is in accordance with an earlier report by Hergot (Herget W F. 1982. "Remote and Cross-stack Measurement of Stack Gas Concentrations using a Mobile FT-IR System," *Appl. Optics,* 21:635-642.), and which is also consistent with an experimentalist's "rule of thumb" that the active method is typically about 3 orders of magnitude more sensitive than a passive measurement. Interestingly, the sensitivity of the inventive technique operated near 380 K appears to be near the geometric mean between the two other methods.

Table 2 also shows good linear trends and general agreement for the concentrations as derived by the active and inventive techniques. This is true for a series of measurements using any one technique, but also that the three techniques quantify the release concentration changes well. The only exception to this was for the final experiments when the start carts had been turned off and only the blowers were used to force the air carrier gas through the stack. In this experiment, the nominal CO release concentration was 5,000 ppmV. The active and inventive measurements agreed quite well and there were measured concentrations of 1,360 ppmV and 1,114 ppmV, respectively, both assuming a 30-cm plume width. The estimated detection limits were 7.97 and 160 ppmV, respectively, for the active and inventive techniques. For the passive measurements, however, the stack release temperature was 63° C., and the ambient background temperature was 32.4° C. By the time that the plume traversed the FOV of the spectrometer, the plume had cooled sufficiently such that it could barely be distinguished above the noise in FIGS. 10-12. As the thermal contrast between the plume and background diminishes, the spectral signature approaches zero. Referring back to FIG. 12, the weak CO thermal emission can barely be recognized above the ambient background, again emphasizing the advantage of the engineered spectral contrast of the inventive technique.

Figure 13:
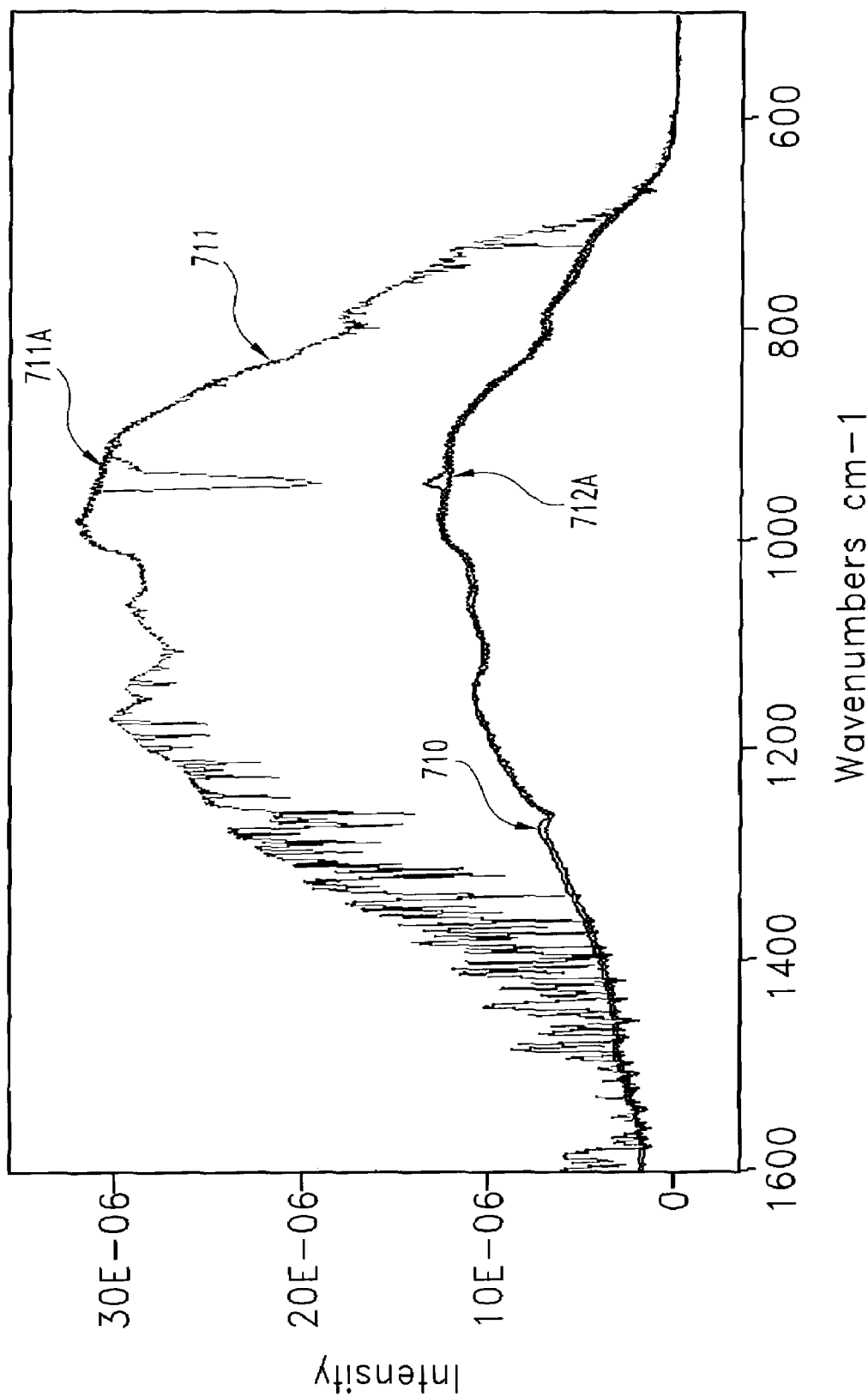
FIG. 13 sets forth LWIR spectra 711, 712 recorded using the inventive and purely passive techniques, respectively. The spectra are GR21/GR19 for the inventive techniques and SK21/SK19 for the passive measurements, respectively. The baseline (no analyte) spectra are particularly evident at one location 711A, 712A in each spectrum. The $SF_6$ peak can be seen at 948 cm$^{-1}$ in both the inventive and passive spectra.

It is also of interest to consider the data that were recorded in the LWIR as well as the MWIR region. Although no LWIR-signature chemicals had quantified releases during these segments, there was an unquantified release during these segments of a chemical with strong LWIR absorptions, namely sulfur hexafluoride, $SF_6$. The $SF_6$ releases were primarily to assist in sighting the plume. Nevertheless, we can easily observe the raw signals for both the inventive and passive techniques in the LWIR region as they are plotted in FIG. 13 and qualitatively gauge the much stronger signal seen by the inventive method. In the figure, the $SF_6$ signal is seen to be in emission mode in passive FTIR (trace 710) and in absorption mode in inventive FTIR (trace 711). The griddle has in this case created a temperature background significantly hotter than the $SF_6$-laden plume. Indeed, visual inspection shows that the $SF_6$ is at some temperature (likely about 50° C.) that is hotter than the passive sky background yet significantly colder than the 110° C. griddle temperature. We reiterate that were the background to be at exactly the same temperature as the plume (assuming approximately equal emissivities), the IR signature of the chemical would not be visible by the passive technique.

It is worth noting that IR measurements in the LWIR region (7 to 13 μm) are typically made at spectral resolutions lower than 1 $cm^{-1}$ used in this experiment, e.g., 4 or 8 $cm^{-1}$. The resolution one chooses to use depends on several parameters, including observation distance, measurement time, spectrometer design, or the analyte(s) of interest. The present noise studies are not comparable to all 22 possible measurement scenarios, but the sensitivities one obtains at 1 $cm^{-1}$ resolution and about 150 seconds acquisition time are comparable to the sensitivities one might obtain from a 4 $cm^{-1}$ resolution measurement and perhaps 5 to 10 second averaging time (albeit at higher specificity). FIG. 10 is a good example from the LWIR region as to how the temperature difference determines the magnitude of the chemical plume signal.

DISCUSSION OF EXPERIMENTAL RESULTS

Figure 14:
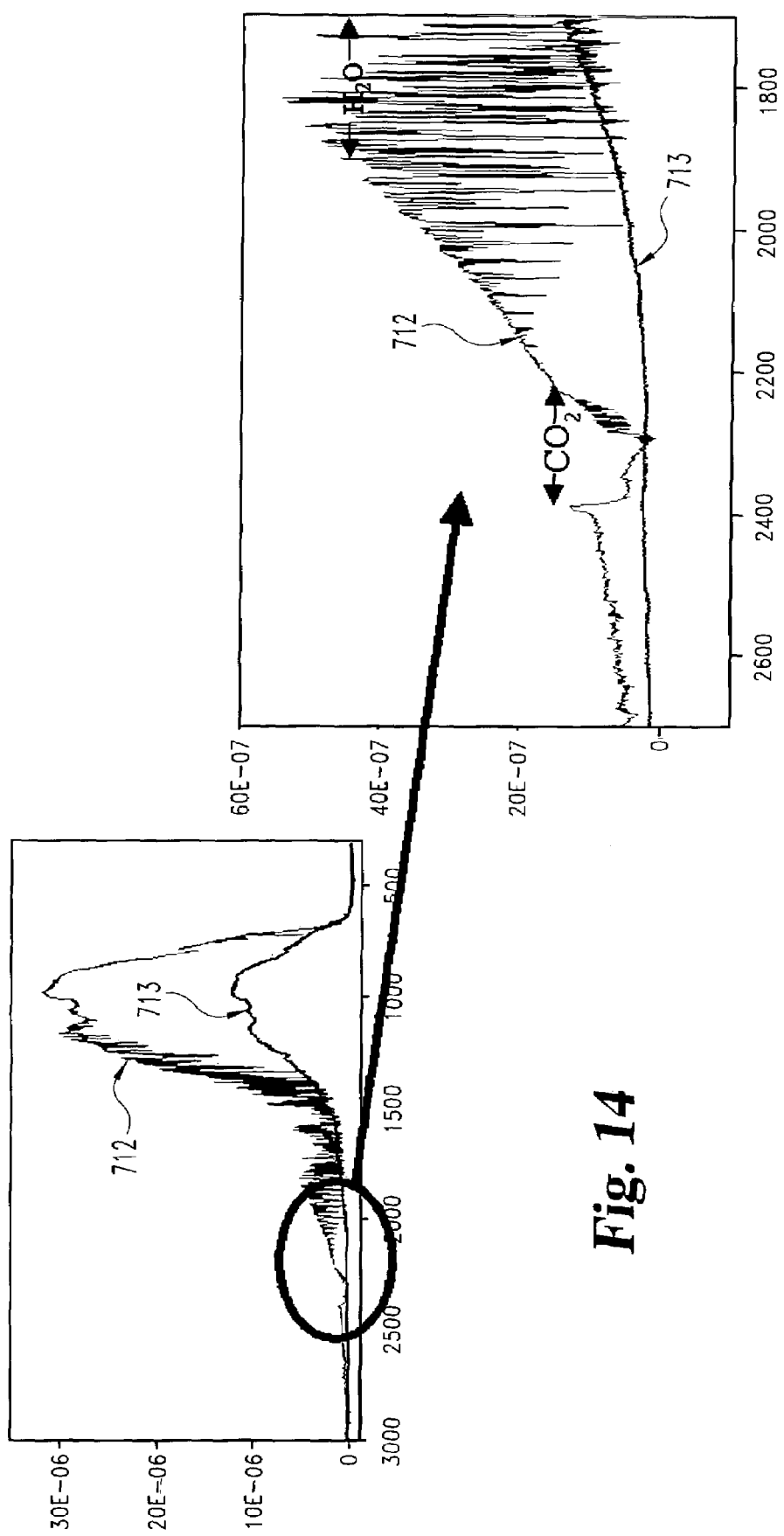
FIG. 14 depicts relative spectrometer response when viewing the passive and inventive sources, i.e., the sky and griddle, respectively. Measurement conditions were identical and the y-axis is the same for both. The inset shows the 1700-2700 cm$^{-1}$ region expanded for clarity, with $H_2O$ and $CO_2$ interfering absorptions noted on plot.

In view of the above, it is seen that the inventive system not only has a significant sensitivity advantage over conventional passive detection techniques, but also has a large spectral advantage compared to passive FTIR since it further extends the broadband coverage from 650 to 1300 $cm^{-1}$ to an extended range of 650 to about 2800 $cm^{-1}$, by providing more IR amplitude in the MIWR region as shown in FIG. 14. This figure represents the FTIR spectrometer responses when looking at the different backgrounds, namely the sky (i.e., passive technique) and the griddle source. In FIG. 14, the spectrum produced by the inventive system is depicted as trace 712, and the spectrum produced by the passive technique is depicted as trace 713. FIG. 14 also shows that in the LWIR there is approximately a factor of 3 greater signal in the LWIR between 700 and 1300 $cm^{-1}$ (near 10 μm), which greatly decreases the measurement time to obtain the same sensitivity (9-fold in the shot-noise limit). There are a host of compounds that can be monitored in this LWIR region, including many organics such as halogenated organics, polyaromatic hydrocarbons, and organophosphorous (pesticide) compounds. The inventive technique thus represents an order of magnitude improvement in signal acquisition time in the LWIR region. The faster response of inventive methods clearly provides a large technological advantage over passive techniques.

The significance of the increase in signal in the MWIR region near 5 μm (=2000 $cm^{-1}$) is clearly shown by the spectra in FIG. 14, as enlarged in the inset, which shows that there is approximately 7 times more IR intensity in this region, which corresponds to a vastly reduced acquisition time for the same signal/noise ratio. The regions between 1350 to 1850 $cm^{-1}$ and 2300 to 2400 $cm^{-1}$ are normally, not used because any signature signals are obscured by $H_2O$ and $CO_2$, respectively. However, the regions in between, namely the MWIR between 1850 to 2300 $cm^{-1}$ and 2400 to 2800 $cm^{-1}$ are relatively free of interferants and can clearly provide much useful information for environmental monitoring of pollutant compounds. Specifically, there are several highly toxic compounds that can be monitored with far better sensitivity in the MWIR regions since they have few or no absorption bands in the long-wave IR. This list includes many gas-phase corrosive acids, such as HI, HCl, HBr, and $SO_2$ (which forms $H_2SO_4$ in the lungs). In addition several common small-molecule toxins have their strongest signatures in this region, including CO, NO, $PH_3$, $AsH_3$, and $Ni(CO)_4$, as well as cyanide and several derivative compounds, including HCN itself, cyanogen (NCCN), and tetracyanoethylene. Many of these species can be monitored only poorly at LWIR wavelengths, and most not at all; i.e., they simply would not be detected in the LWIR because they have no signature in that region. As opposed to the typically more sensitive laser methods, the Fourier transform nature of the inventive method means a wide variety of compounds can be monitored simultaneously using both the enhanced sensitivity in the LWIR as well as the "added" spectral domain of the MWIR.

In view of the above description, a person of ordinary skill in the art will appreciate that the invention provides the advantage of enhanced sensitivity of IR detection of toxic gases compared to passive IR detection techniques, while also enabling the detection of gases whose absorptions lie in wavelength domains not normally accessible to passive IR spectroscopy. The system thus not only has a broadband sensitivity advantage, but also removes some of the limitations of passive FTIR by further extending the broadband coverage to about 2700 $cm^{-1}$ rather than only 650 to 1300 $cm^{-1}$. Furthermore, the invention provides the additional advantage of eliminating the requirement of precise and continuous alignment of optical components as is necessary in active IR detection systems.

The inventive technique finds advantageous use in a wide variety of applications, including, for example, signature analysis, high-value facility protections and homeland defense applications. For example, a possible location for an inventive system is in an air shaft of a building, wherein the system is capable of testing the building's air supply, while being contained in an all-metal housing. Inventive techniques advantageously generate and maintain a significant temperature difference ΔT relative to a gas plume. By providing a background of sufficiently hot temperature, inventive systems ensure that the plume temperature is colder than the background temperature for any gas that is released near ambient temperature or has equilibrated to near ambient temperature (typically about 25° C.). The background temperature provided by the griddle was typically 110° C., thus providing a ΔT of approximately 80° C. This corresponds to one to two orders of magnitude greater sensitivity as compared to typical ambient (passive) measurements. Although not as sensitive as an active technique, the pointing/stability requirements of either trying to align two telescopes or separating a retro-reflected beam are removed. The detecting spectrometer is simply aimed at the hot source, and alignment is simplified due to the large IR signal provided by the source (the griddle is in fact a good approximation to a blackbody at 400 K).

While the invention has been described in detail in the foregoing description, the same is to be considered as illustrative and not restrictive in character, it being understood that only selected embodiments have been described and that all changes, equivalents, and modifications that come within the spirit of the invention described herein or defined by the following claims are desired to be protected. Any experiments, experimental examples, or experimental results provided herein are intended to be illustrative of the present invention and should not be considered limiting or restrictive with regard to the invention scope. Further, any theory, mechanism of operation, or finding stated herein is meant to further enhance understanding of the present invention and is not intended to limit the present invention in any way to such theory, mechanism or finding. All publications, patents, and patent applications cited in this specification are herein incorporated by reference as if each individual publication, patent, or patent application were specifically and individually indicated to be incorporated by reference and set forth in its entirety herein.

What is claimed is:

1. A system for remotely detecting at least one constituent of a gas, comprising:
   a spectrally sensitive receiver positioned at a receiver location, said receiver including an optical component defining a field of view; and
   a first extended source of broadband infrared radiation positioned at a first source location separated from the receiver location, the first source comprising a surface and a heating component thermally coupled to the surface; wherein the heating component is configured to heat the surface to a temperature above ambient temperature; and wherein the first source and the receiver are oriented such that at least a portion of the surface of the first source is in the field of view;
   wherein the receiver is operable to collect spectral infrared absorption data representative of a first gas present between the first source and the receiver, the heating component being operatively coupled to a temperature controller; and
   further comprising a temperature sensor operative to sense ambient temperature, wherein the temperature controller is operative to control the heating component such that the heating component heats the surface to a substantially uniform temperature that is a predetermined number of degrees higher than ambient temperature sensed by the temperature sensor.

2. The system in accordance with claim 1 wherein the temperature sensor, the temperature controller and the receiver are operatively coupled to a processing subsystem.

3. The system in accordance with claim 1 wherein the substantially uniform temperature is a temperature of from about 10 to about 300° C. higher than ambient temperature.

4. The system in accordance with claim 1 wherein the substantially uniform temperature is a temperature of from about 20 to about 200° C. higher than ambient temperature.

5. The system in accordance with claim 1 wherein the substantially uniform temperature is a temperature of from about 50 to about 150° C. higher than ambient temperature.

6. The system in accordance with claim 1 wherein the substantially uniform temperature is a temperature of from about 75 to about 125° C. higher than ambient temperature.

7. A method for remotely analyzing a gas, comprising:
   providing a spectrally sensitive receiver at a receiver location, the receiver including an optical component defining a field of view;
   providing a first extended source of broadband infrared radiation at a first source location separated from the receiver location by a first distance, the first source comprising a surface and a heating component thermally coupled to the surface; wherein the heating component is configured to heat the surface to a temperature above ambient temperature; and wherein the first source and the receiver are oriented such that at least a portion of the surface of the first source is in the field of view;
   collecting spectral infrared absorption data with the receiver, the data being representative of a first gas present between the first source and the receiver; and
   comparing the data representative of the first gas to known gas infrared absorption information to determine at least one characteristic of the first gas; further comprising providing a temperature sensor operative to sense ambient temperature, and controlling the heating component such that the heating component heats the surface to a substantially uniform temperature that is a predetermined number of degrees higher than ambient temperature sensed by the temperature sensor.

8. The method in accordance with claim 7 wherein the temperature sensor, the temperature controller and the receiver are operatively coupled to a processing subsystem.

9. The method in accordance with claim 7 wherein the substantially uniform temperature is a temperature of from about 10 to about 300° C. higher than ambient temperature.

10. The method in accordance with claim 7 wherein the substantially uniform temperature is a temperature of from about 20 to about 200° C. higher than ambient temperature.

11. The method in accordance with claim 7 wherein the substantially uniform temperature is a temperature of from about 50 to about 150° C. higher than ambient temperature.

12. The method in accordance with claim 7 wherein the substantially uniform temperature is a temperature of from about 75 to about 125° C. higher than ambient temperature.

* * * * *

UNITED STATES PATENT AND TRADEMARK OFFICE
CERTIFICATE OF CORRECTION

PATENT NO. : 7,301,148 B2
APPLICATION NO. : 10/422027
DATED : November 27, 2007
INVENTOR(S) : Timothy J. Johnson It is certified that error appears in the above-identified patent and that said Letters Patent is hereby corrected as shown below:

In the Specification:

Column 1, line 52, "TR beam." should read --IR beam.--.

Column 15, line 21, "MWFR" should read --MWIR--.

Column 16, line 51, "ficht" should read --light--.

Column 17, line 17, "$10^{31}$ $^{17}$" should read --$10^{-17}$--.

Column 26, line 16, "temperatures Although" should read --temperatures. Although--.

Column 27, line 47, "cm to" should read --$cm^{-1}$ to--.

Signed and Sealed this

Sixteenth Day of March, 2010

David J. Kappos
*Director of the United States Patent and Trademark Office*